(12) United States Patent
Suzuki

(10) Patent No.: US 8,251,951 B2
(45) Date of Patent: Aug. 28, 2012

(54) INJECTION NEEDLE CARTRIDGE AND INJECTOR

(75) Inventor: Ichiro Suzuki, Nagoya (JP)

(73) Assignee: Suzuken Company Limited, Nagoya-shi (JP)

( * ) Notice: Subject to any disclaimer, the term of this patent is extended or adjusted under 35 U.S.C. 154(b) by 510 days.

(21) Appl. No.: 12/518,926

(22) PCT Filed: Dec. 13, 2007

(86) PCT No.: PCT/JP2007/074065
§ 371 (c)(1),
(2), (4) Date: Jun. 12, 2009

(87) PCT Pub. No.: WO2008/072715
PCT Pub. Date: Jun. 19, 2008

(65) Prior Publication Data
US 2010/0042047 A1    Feb. 18, 2010

(30) Foreign Application Priority Data
Dec. 13, 2006 (JP) .................................. 2006-336413

(51) Int. Cl.
*A61M 5/00* (2006.01)
*A61M 37/00* (2006.01)
*A61M 5/32* (2006.01)

(52) U.S. Cl. ........ 604/110; 604/117; 604/136; 604/192; 604/195; 604/198

(58) Field of Classification Search .................. 604/110, 604/117, 192, 198, 232
See application file for complete search history.

(56) References Cited

U.S. PATENT DOCUMENTS
5,292,314 A    3/1994 D'Alessio et al.
(Continued)

FOREIGN PATENT DOCUMENTS
JP    03-139363 A    6/1991
(Continued)

*Primary Examiner* — Christopher D Koharski
*Assistant Examiner* — Ian Holloway
(74) *Attorney, Agent, or Firm* — Westerman, Hattori, Daniels & Adrian, LLP

(57) ABSTRACT

The invention provides a cartridge-type injection needle and injector. The injection needle cartridge has a substantially columnar retaining member for retaining the injection needle penetrating therethrough and a pair of holder members forming a containing space for containing the retaining member. The paired holding members are formed by a first holder member having a first bottom plate and a first slider section and a second holder member having a second bottom plate facing to the first bottom plate and a second slider section. The containing space is axially extendable and retractable in the state in which the slider sections are alternately displaced along the outer periphery of the retaining member and is not axially retractable in the state in which the extreme end faces of the slider sections face to each other.

16 Claims, 20 Drawing Sheets

U.S. PATENT DOCUMENTS

| | | |
|---|---|---|
| 5,403,286 A | 4/1995 | Lockwood, Jr. |
| 5,429,612 A | 7/1995 | Berthier |
| 5,718,239 A | 2/1998 | Newby et al. |
| 6,203,529 B1 | 3/2001 | Gabriel et al. |
| 6,213,977 B1 * | 4/2001 | Hjertman et al. ............. 604/117 |
| 6,391,003 B1 * | 5/2002 | Lesch, Jr. .................... 604/110 |
| 6,547,764 B2 | 4/2003 | Larsen et al. |
| 6,986,760 B2 | 1/2006 | Giambattista et al. |
| 2003/0078546 A1 * | 4/2003 | Jensen ......................... 604/232 |
| 2003/0105430 A1 | 6/2003 | Lavi et al. |
| 2003/0199822 A1 | 10/2003 | Alchas et al. |
| 2005/0038392 A1 | 2/2005 | DeSalvo |

FOREIGN PATENT DOCUMENTS

| | | |
|---|---|---|
| JP | 6-31747 U | 4/1994 |
| JP | 2001-523485 A | 11/2001 |
| WO | WO 01/91837 A1 | 12/2001 |
| WO | WO 02/09797 A1 | 2/2002 |
| WO | WO 03/045480 A1 | 6/2003 |

* cited by examiner

INJECTION NEEDLE CARTRIDGE AND INJECTOR

TECHNICAL FIELD

The present invention relates to a disposable cartridge-type injection needle.

BACKGROUND ART

In order to alleviate a burden of hospital visit on a patient such as a diabetic requiring everyday medication, there have conventionally been available portable injectors for the patient to administer an injection by himself/herself in the home, workplace, and the like. For such an injector, a disposable cartridge-type injection needle has sometimes been used to prevent infection and the like caused by the secondary use of the injection needle (for example, refer to Patent Document 1).

The above-described conventional cartridge-type injection needle has problems as described below. That is to say, there arises a problem in that when the cartridge-type injection needle is mounted to or removed from an injector body, a needle stick accident may happen. Further, a used injection needle has a problem in that secondary infection caused by a needle stick accident and the like may occur.

Patent Document 1: Japanese Patent Laid-Open No. 8-66475

DISCLOSURE OF THE INVENTION

Problems to be Solved by the Invention

The present invention has been made to solve the above problems, and accordingly an object thereof is to provide a highly safe cartridge-type injection needle and injector not causing a needle stick accident and the like.

Means for Solving the Problems

A first aspect of the present invention provides an injection needle cartridge including:

a substantially columnar retaining member for retaining an injection needle axially penetrating therethrough so that the injection needle projects from both end surfaces thereof;

a first holder member having a first bottom plate facing to one end surface of the retaining member and a first slider section erected from the first bottom plate so as to be in contact with the outer peripheral side surface of the retaining member to hold the retaining member;

a second holder member having a second bottom plate facing to the other end surface of the retaining member and a second slider section erected from the second bottom plate so as to be in contact with the outer peripheral side surface of the retaining member to hold the retaining member, wherein the second holder member is configured to contain the retaining member in a containing space formed by the first bottom plate and the second bottom plate oriented to face to each other, and to be rotatable relative to the first holder member about the axis of the retaining member; and a substantially cylindrical inner ring constituting a rotation restricting mechanism for restricting the relative rotation of the paired holder members about the axis of the retaining member in a state of being placed around the retaining member and positioned on the inner periphery side of the first slider section or the second slider section, characterized in that the containing space is axially extendable and retractable in the state in which the slider sections are alternately displaced along the outer periphery of the retaining member, and is not axially retractable in the state in which the extreme end faces of the slider sections face to each other; and the injection needle of the retaining member penetrates through and projects from the bottom surface plates when the containing space is retracted axially.

A second aspect of the present invention provides an injection needle cartridge including:

a substantially columnar retaining member for retaining an injection needle axially penetrating therethrough so that the injection needle projects from both end surfaces thereof;

a first holder member having a first bottom plate facing to one end surface of the retaining member and a first slider section erected from the first bottom plate so as to be in contact with the outer peripheral side surface of the retaining member to hold the retaining member;

a second holder member having a second bottom plate facing to the other end surface of the retaining member and a second slider section erected from the second bottom plate so as to be in contact with the outer peripheral side surface of the retaining member to hold the retaining member, wherein the second holder member is configured to contain the retaining member in a containing space formed by the first bottom plate and the second bottom plate oriented to face to each other, and to be rotatable relative to the first holder member about the axis of the retaining member; and a substantially cylindrical surrounding ring constituting a rotation restricting mechanism for restricting the relative rotation of the paired holder members in a state of being placed around the first and second slider sections, characterized in that the containing space is axially extendable and retractable in the state in which the slider sections are alternately displaced along the outer periphery of the retaining member, and is not axially retractable in the state in which the extreme end faces of the slider sections face to each other; and the injection needle of the retaining member penetrates through and projects from the bottom surface plates when the containing space is retracted axially.

The injection needle cartridges of the first and second aspects of the present invention each include the retaining member for retaining the injection needle axially penetrating therethrough, the first holder member having the first slider section erected from the first bottom plate, and the second holder member having the second slider section erected from the second bottom plate.

The paired holder members contain the retaining member in the containing space formed by causing the first and second bottom plates to face to each other, and can turn relative to each other about the axis of the retaining member contained in the containing space. In the above-described injection needle cartridge, the containing space is axially extendable and retractable in the state in which the first and second slider sections are alternately displaced along the outer periphery of the retaining member. By retracting the containing space, the injection needle is projected penetrating the bottom plates. On the other hand, in the injection needle cartridge, by causing the extreme end faces of the first and second slider sections to face to each other, a state in which the containing space is not axially retractable can be formed.

That is to say, in the injection needle cartridge of the first aspect of the present invention, by changing the relative rotation position of the paired holder members, switching can be performed with high reliability between the extendable/retractable state in which the injection needle can be projected or withdrawn and the not retractable state in which the injection needle does not project. Therefore, according to the above-described injection needle cartridge, by setting the not retractable state, the injection needle can be stored in the containing space reliably, so that a needle stick accident and the like can be prevented with high reliability.

Furthermore, by using the rotation restricting mechanism provided on the inner ring or the surrounding ring to restrict the relative rotation of the paired holder members, it is possible to prevent a possibility that, for example, the injection needle cartridge, which would have been set to a state of not axially retractable, changes inadvertently to the retractable state. If the possibility of the retractable state being set inadvertently can be prevented, the occurrence of a needle stick accident and the like can be avoided with high reliability.

As described above, the injection needle cartridges of the first and second aspects of the present invention are excellent, highly safe products that can prevent a needle stick accident and the like.

A third aspect of the present invention provides an injector including:

an injection needle cartridge including a substantially columnar retaining member for retaining an injection needle axially penetrating therethrough so that the injection needle projects from both end surfaces thereof; a first holder member having a first bottom plate facing to one end surface of the retaining member and a first slider section erected from the first bottom plate so as to be in contact with the outer peripheral side surface of the retaining member to hold the retaining member; a second holder member having a second bottom plate facing to the other end surface of the retaining member and a second slider section erected from the second bottom plate so as to be in contact with the outer peripheral side surface of the retaining member to hold the retaining member, wherein the second holder member is configured to contain the retaining member in a containing space formed by the first bottom plate and the second bottom plate oriented to face to each other, and to be rotatable relative to the first holder member about the axis of the retaining member; and a substantially cylindrical inner ring constituting a rotation restricting mechanism for restricting the relative rotation of the paired holder members in a state of being placed around the retaining member and being positioned on the inner periphery side of the first or second slider section, wherein the containing space is axially extendable and retractable in the state in which the slider sections are alternately displaced along the outer periphery of the retaining member, and is not axially retractable in the state in which the extreme end faces of the slider sections face to each other; and the injection needle of the retaining member penetrates through and projects from the bottom surface plates when the containing space is retracted axially;

a body part that contains a medicine and is provided with a front end surface for allowing one side of the injection needle of the injection needle cartridge to be pierced; and a cap section that is a bottomed substantially cylindrical member placed around the front end side of the body part and is provided with a through hole for allowing the other side of the injection needle of the internally accommodated injection needle cartridge to penetrate through, characterized in that the cap section is configured to enable the paired holder members to turn relative to each other and to be capable of advancing and retreating to axially retract the containing space with respect to the body part.

A fourth aspect of the present invention provides an injector including:

an injection needle cartridge including a substantially columnar retaining member for retaining an injection needle axially penetrating therethrough so that the injection needle projects from both end surfaces thereof; a first holder member having a first bottom plate facing to one end surface of the retaining member and a first slider section erected from the first bottom plate so as to be in contact with the outer peripheral side surface of the retaining member to hold the retaining member; a second holder member having a second bottom plate facing to the other end surface of the retaining member and a second slider section erected from the second bottom plate so as to be in contact with the outer peripheral side surface of the retaining member to hold the retaining member, wherein the second holder member is configured to contain the retaining member in a containing space formed by the first bottom plate and the second bottom plate oriented to face to each other, and to be rotatable relative to the first holder member about the axis of the retaining member; and a substantially cylindrical surrounding ring constituting a rotation restricting mechanism for restricting the relative rotation of the paired holder members in a state of being placed around the first and second slider sections about the axis of the retaining member, wherein the containing space is axially extendable and retractable in the state in which the slider sections are alternately displaced along the outer periphery of the retaining member, and is not axially retractable in the state in which the extreme end faces of the slider sections face to each other; and the injection needle of the retaining member penetrates through and projects from the bottom surface plates when the containing space is retracted axially;

a body part that contains a medicine and is provided with a front end surface for allowing one side of the injection needle of the injection needle cartridge to be pierced; and a cap section that is a bottomed substantially cylindrical member placed around the front end side of the body part and is provided with a through hole for allowing the other side of the injection needle of the internally accommodated injection needle cartridge to penetrate through, characterized in that the cap section is configured to enable the paired holder members to turn relative to each other and to be capable of advancing and retreating to axially retract the containing space with respect to the body part.

The injectors of the third and fourth aspects of the present invention use the highly safe injection needle cartridge of the first or second aspect of the present invention. Therefore, this injector has little possibility that a needle stick accident and the like occurs, for example, when the injection needle cartridge is removed after being used or after it has been removed.

As described above, the injectors of the third and fourth aspects of the present invention are highly safe products that can prevent a needle stick accident and the like.

DESCRIPTION OF SYMBOLS

Figure 1:
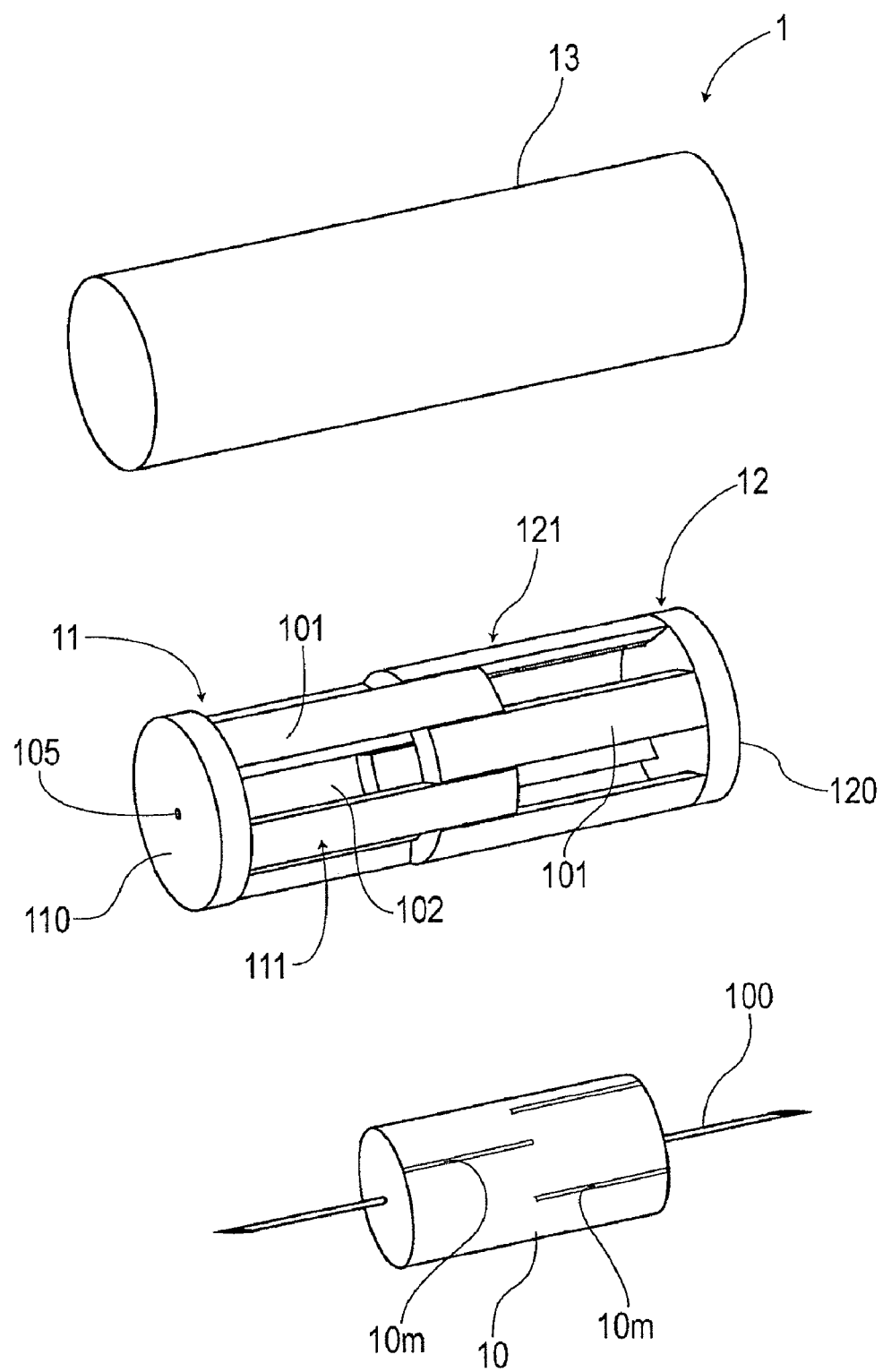
FIG. 1 is a perspective view showing a configuration of an injection needle cartridge in example 1.

1 injection needle cartridge
10 retaining member
100 injection needle
102 containing space
110, 120 bottom plate
111, 121 slider section
2 medication pen
20 barrel
220 membrane
23 dosage setting mechanism
24 medicine cartridge
31 inner ring
32 outer ring

BEST MODE FOR CARRYING OUT THE INVENTION

In the first and second aspects of the present invention, the injection needle cartridge is preferably configured to be in the not axially retractable state when being in an unused state, be made in the axially retractable state by turning the paired holder members relative to each other when being in use, and be made capable of reestablishing the not axially retractable state by turning the paired holder members relative to each other again after being used; and the rotation restricting mechanism is preferably configured to allow the relative rotation of the paired holder members before the injection needle cartridge shifts to the axially retractable state, and restrict the relative rotation of the paired holder members after the injection needle cartridge shifts from the axially retractable state to the not axially retractable state.

In this case, if the not axially retractable state is formed after the use of the injection needle cartridge, a possibility that the injection needle cartridge shifts again to the axially retractable state can be prevented with high reliability.

Also, the injection needle cartridge preferably has an airtight member for maintaining the sterilized state of the retaining member, and the injection needle cartridge is configured so that the injection needle of the retaining member penetrates through and projects from the airtight member.

In this case, the sterilized state of the retaining member including the injection needle can be kept at a high level by the airtight member. Therefore, according to the above-described injection needle cartridge, a possibility of the injection needle being contaminated by various germs can be prevented, and the intrusion of various germs into the human body and the like subjected to injection, which is caused by an injection, can be prevented.

Also, the injection needle cartridge preferably includes an applicator including a substantially cylindrical first member provided with an engagement part engaging with an injector on which the injection needle cartridge is to be mounted and a second member that is provided with a hollow part for allowing the first member to be inserted and advances and retreats in the axial direction with respect to the first member, the applicator being formed so as to be capable of accommodating the paired holder members and the retaining member integrally; and the applicator is preferably configured so that the paired holder members can be turned relatively by turning the second member relative to the first member, and the containing space can be retracted axially by the advance and retreat of the second member with respect to the first member.

The applicator has a function of assisting in mounting of the injection needle cartridge to the injector, a function of relatively rotating the paired holder members, and a function of accommodating the injection needle cartridge. Therefore, in the case where the applicator is used, the mountability of the injection needle cartridge to the injector can be improved remarkably, and also the safety can be improved further.

In the first aspect of the present invention, the injection needle cartridge preferably includes a substantially cylindrical outer ring placed around the first and second slider sections; and the outer ring preferably has an extension restricting mechanism configured so that the maximum axial separation distance of the paired holder members can be restricted in the injection needle cartridge in the axially extendable and retractable state.

In this case, in the injection needle cartridge in the axially extendable and retractable state, by restricting the maximum separation distance of the paired holder members, the state in which the slider sections hold the retaining member can be maintained with high reliability. Therefore, a possibility of the holder member coming off the retaining member can be prevented. If the holder member can be prevented from coming off, the exposure of the injection needle to the outside can be prevented with high reliability, so that the occurrence of a needle stick accident and the like can be avoided.

Also, each of the slider sections preferably has an engagement part that engages with the other of the slider sections in the state in which the extreme end faces of the slider sections face to each other; and the injection needle cartridge is preferably configured so that by engaging the slider sections with each other via the engagement parts, the relative advance and retreat in the axial direction of the paired holder members can be restricted.

In this case, in the injection needle cartridge in the not axially retractable state, a possibility of the paired holder members separating in the axial direction can be prevented. Therefore, the state in which the slider sections hold the retaining member is maintained with high reliability, and therefore the holder member can be prevented from coming off. If the holder member can be prevented from coming off, the exposure of the injection needle to the outside can be prevented with high reliability, so that the occurrence of a needle stick accident and the like can be avoided.

Also, in locations in which the retaining member and the slider sections are in contact with each other, a groove-shaped advance/retreat groove provided along the axial direction and a convex part that advances and retreats in a state of being accommodated in the advance/retreat groove are preferably provided, and the advance/retreat groove is preferably formed so as to prevent the convex part from coming off in the axial direction.

In this case, a possibility that the holder members come off the retaining member, and the injection needle is exposed to the outside can be prevented. Therefore, according to the above-described injection needle cartridge, there can be prevented a needle stick accident and the like that may occur when the holder members are operated so as to extend the containing space in the axial direction.

In the second aspect of the present invention, in each of the holder members, a convex part projecting on the inner periphery side toward the outer peripheral surface of the retaining member is preferably formed on at least either one of the slider sections; and the retaining member preferably has an advance/retreat restricting part capable of restricting the maximum axial separation distance of the paired holder members by means of the engagement with the convex part formed on each of the holder members.

In this case, by the engagement of the advance/retreat restricting part with the convex part, the distance through which the paired holder members can be separated in the axial direction can be restricted, and a possibility of the holder members coming off the retaining member can be prevented. Thereby, the state in which the retaining member is contained between the paired holder members can be maintained with high reliability, and therefore a possibility of the injection needle being exposed to the outside can be prevented.

In the third and fourth aspects of the present invention, as a method for turning the paired holder members relative to each other, there is available a method in which the relative rotation of one holder member and the body part is restricted, and also the relative rotation of the other holder member and the cap section is restricted, and by turning the cap section relative to the body part, the paired holder members are turned relative to each other. Further, as another method, a method in which the cap section provided with a rotatable rotating member is used is available. In this method, if the relative rotation of one holder member and the rotating member is restricted, and also the relative rotation of the other holder member and the cap section body is restricted, the paired holder members can be turned relative to each other according to the rotation of the rotating member.

Also, the injector is preferably provided with a storage section for storing spare injection needle cartridges.

In this case, by storing the spare injection needle cartridges in the storage section, the injection needle cartridges needed, for example, for one-day living can be carried with the user together with the injector.

EXAMPLES

Example 1

Example 1 is an example relating to a disposable injection needle cartridge 1 and an injector 2 using this injection needle cartridge 1. The details thereof are explained with reference to FIGS. 1 to 10.

The injection needle cartridge 1 of this example includes a substantially columnar retaining member 10 for retaining an injection needle 100 axially penetrating therethrough so that the injection needle 100 projects from both end surfaces thereof; a first holder member 11 having a first bottom plate 110 facing to one end surface of the retaining member 10 and a first slider section 111 erected from the first bottom plate 110 so as to be in contact with the outer peripheral side surface of the retaining member 10 to hold the retaining member 10; a second holder member 12 having a second bottom plate 120 facing to the other end surface of the retaining member 10 and a second slider section 121 erected from the second bottom plate 120 so as to be in contact with the outer peripheral side surface of the retaining member 10 to hold the retaining member 10, which second holder member contains the retaining member 10 in a containing space 102 formed by causing the first bottom plate 110 and the second bottom plate 120 to face to each other, and is rotatable relative to the first holder member 11 about the axis of the retaining member 10; and a substantially cylindrical inner ring 31 constituting a rotation restricting mechanism for restricting the relative rotation of the paired holder members 11 and 12 about the axis of the retaining member 10 in a state of being placed around the retaining member 10 and positioned on the inner periphery side of the first slider section 111 or the second slider section 121.

The containing space 102 is axially extendable and retractable in the state in which the slider sections 111 and 121 are alternately displaced along the outer periphery of the retaining member 10, and is not axially retractable in the state in which the extreme end faces of the slider sections 111 and 121 face to each other.

When the containing space 102 is retracted axially, the injection needle 100 of the retaining member 10 penetrates through and projects from the bottom surface plates 110 and 120.

This configuration is explained in more detail below.

In the explanation of this example, first, three kinds of first to third embodiments are explained, and then, an embodiment of this example is explained based on the third embodiment explained finally.

Figure 2:
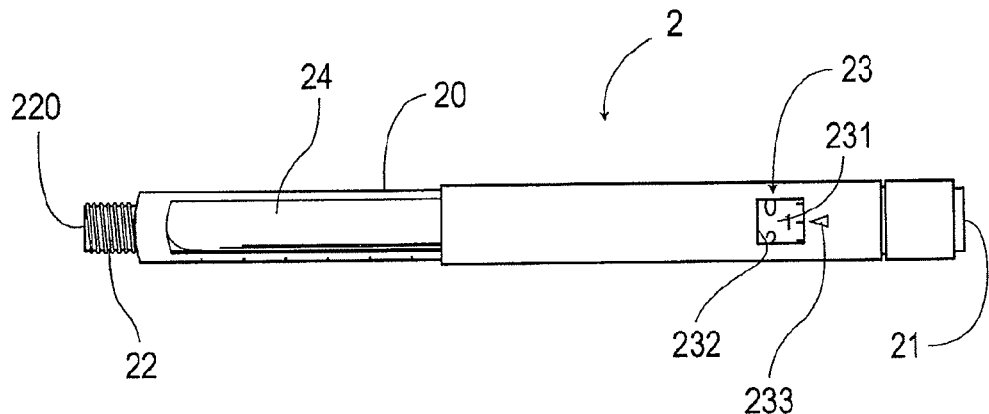
FIG. 2 is a side view of a medication pen in example 1.

First, the first embodiment is explained with reference to FIGS. 1 to 8. As shown in FIGS. 1 and 2, the injector 2 of the first embodiment is a pen-type hypodermic injector generally called a medication pen. The injector 2 of this type (hereinafter, referred to as a medication pen 2) is used, for example, for a patient such as a diabetic requiring medication every fixed time to administer an injection by himself/herself. That is to say, the medication pen 2 is used to administer an injection by mounting the above-described disposable injection needle cartridge 1.

As shown in FIG. 2, the medication pen 2 includes a substantially cylindrical barrel 20 forming a body part; a medicine cartridge 24 for containing a liquid medicine of several doses; a push rod 21 that is a pushing operation part for injecting the medicine; and a dosage setting mechanism 23 for beforehand setting the dosage of medicine used by one injection.

As shown in FIGS. 1 and 2, at the outer periphery of the extreme end portion of the barrel 20, there is formed a threaded part 22 for internally installing the medication pen 2 to an applicator 15 (described later) for holding the injection needle cartridge 1. At the front end of the barrel 20 corresponding to the inner periphery side of the threaded part 22, a rubber membrane 220 capable of being stuck and resealed is provided. At the rear end, that is, the opening end of the barrel 20, the push rod 21 for injecting the medicine is provided. The push rod 21 is configured so that the medicine can be injected by an axially pushing operation.

The medicine cartridge 24 is a substantially cylindrical container inserted in the barrel 20. The end face on the membrane 220 side of the medicine cartridge 24 is configured to be capable of being pressed against the membrane 220 in a fluid tight state. On the other hand, the end portion on the push rod 21 side of the medicine cartridge 24 is an opening end, and a plunger (not shown) is inserted at this opening end in a fluid tight state so as to be capable of being advanced and retreated. This plunger advances in a stroke manner toward the front end side of the barrel 20 according to the pushing operation of the push rod 21.

The dosage setting mechanism 23 is a mechanism for beforehand setting the advance stroke of the plunger caused by the pushing operation of the push rod 21. This dosage setting mechanism 23 is configured by combining an observation window 232 formed in the outer peripheral portion close to the rear end of the substantially cylindrical barrel 20 with a thin-walled and substantially cylindrical dial sleeve 231 arranged in a clearance between the medicine cartridge 24 and the barrel 20.

The dosage setting mechanism 23 has a reference line 233 printed along the axial direction on the outer peripheral surface of the barrel 20 and numerals and scale representing the dosage of 0, 1, 2 . . . printed at the outer periphery of the dial sleeve 231. In this dosage setting mechanism 23, the numerals and scale on the dial sleeve 231 can be observed visually via the observation window 232 of the barrel 20. By turning the dial sleeve 231, the numeral and scale corresponding to the dosage can be caused to coincide with the reference line 233 at the outer periphery of the barrel 20. According to this dosage setting mechanism 23, by the turning operation of the dial sleeve 231, the advance stroke amount of plunger at the time of injection is set, by which an exact dosage can be set beforehand.

Next, the above-described injection needle cartridge 1 is explained with reference to FIGS. 1 to 7. As described above referring to FIG. 1, the injection needle cartridge 1 has the substantially columnar retaining member 10 for retaining the injection needle 100 penetrating therethrough, the first holder member 11 including the first bottom plate 110 and the first slider section 111, and the second holder member 12 including the second bottom plate 120 and the second slider section 121. In this injection needle cartridge 1, the pair of holder members 11 and 12 containing the retaining member 10 are covered wholly by a film 13 consisting of polypropylene, by which the sterilized state of the injection needle 100 is maintained. As the film 13, besides polypropylene, various materials such as polyethylene, polyvinylidene chloride, and polyethylene terephthalate can be used.

Figure 3:
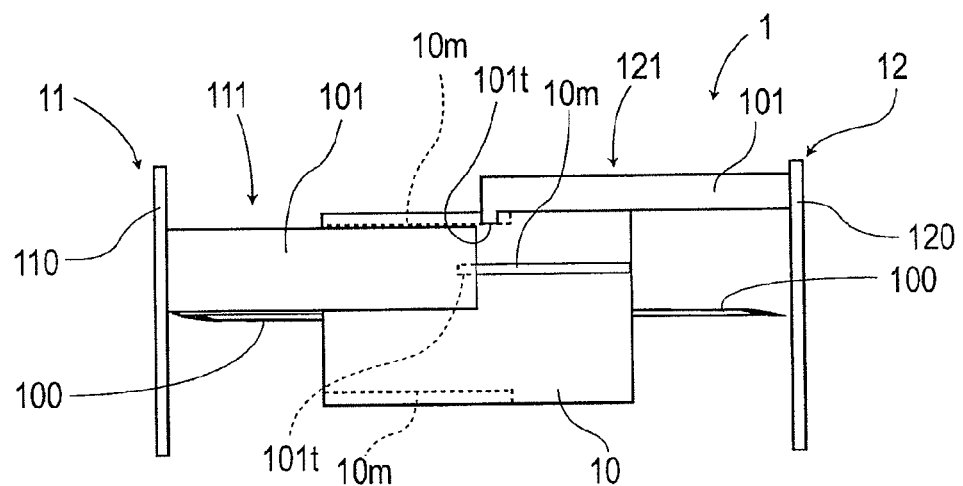
FIG. 3 is a side view of a pair of holder members and a retaining member showing an axially retractable state in example 1.

As shown in FIGS. 1 and 3, the retaining member 10 is a substantially columnar member measuring about 4 mm in diameter and 28 mm in length formed of polypropylene, and the stainless steel injection needle 100 is penetratingly arranged along the center axis thereof. The injection needle 100 projects 5 mm respectively from both end sides of the retaining member 10, and has needle points at both ends thereof. One of the needle points is a needle point for piercing into the human body's skin or the like, which is a portion subjected to injection, and the other of the needle points is a needle point for piercing into the membrane 220 of the medication pen 2. Further, as shown in FIG. 1 and FIGS. 3 to 5, the retaining member 10 is formed with guide grooves 10m each having a concave cross section for guiding the axial sliding operation of the slider sections 111 and 121 at eight places in the circumferential direction in the outer peripheral surface thereof.

As the material for the injection needle 100, besides stainless steel, a resin material can be used. In the case of the injection needle 100 formed of a resin, the disposal thereof after use is easier. Further, if the injection needle 100 is formed of a biodegradable plastic or the like material, the disposal can be made far easier, which can prevent a possibility of harming the environment.

Each of the holder members 11 and 12 is a component formed of polypropylene. The bottom plate 110, 120 constituting the holder member 11, 12 is a substantially disc-shaped part having a diameter of about 10 mm and a thickness of 1 mm, and a through hole 105 through which the injection needle 100 penetrates is formed along the axis thereof as shown in FIG. 1 and FIGS. 3 to 5. The slider section 111, 121 consists of a plurality of pillar-shaped parts 101 erected from the outer periphery portion of the bottom plate 110, 120. In this example, the slider section 111, 121 has four pillar-shaped parts 101 in the circumferential direction.

As the through hole 105, a completely penetrating hole is used. Instead, a thin film may be formed in the through hole 105 when the holder member 11, 12 is molded. In this case, in place of the film 13 (refer to FIG. 1) covering the whole of the injection needle cartridge 1, a film that covers only the outer peripheral side surface excluding both the end surfaces of the injection needle cartridge 1 can be adopted. If this film covering the outer peripheral side surface is combined with the thin film in the through hole 105, like the above-described film 13, the sterilized state of the injection needle 100 can be maintained with high reliability.

As the shape of the bottom plate 110, 120, in place of the disc shape, a polygonal shape such as a hexagonal shape or an octagonal shape may be used. In this case, the holder member 11, 12 is prevented from rolling when it is removed from the applicator 15, so that a possibility of the holder member 11, 12 dropping from a worktable or the like can be prevented.

Furthermore, as the material for the retaining member 10 and the holder members 11 and 12, besides polypropylene, various materials such as polyethylene, polyurethane, and polyethylene terephthalate can be used. Further, the retaining member 10 and the holder members 11 and 12 may also be formed of a biodegradable plastic. In this case, the disposal of the injection needle cartridge 1 can be made far more easily.

Figure 4:
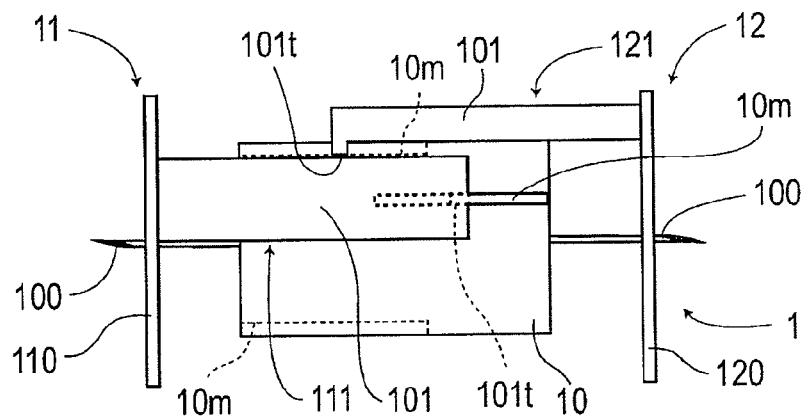
FIG. 4 a side view of a pair of holder members and a retaining member showing a state of being axially retracted in example 1.
Figure 5:
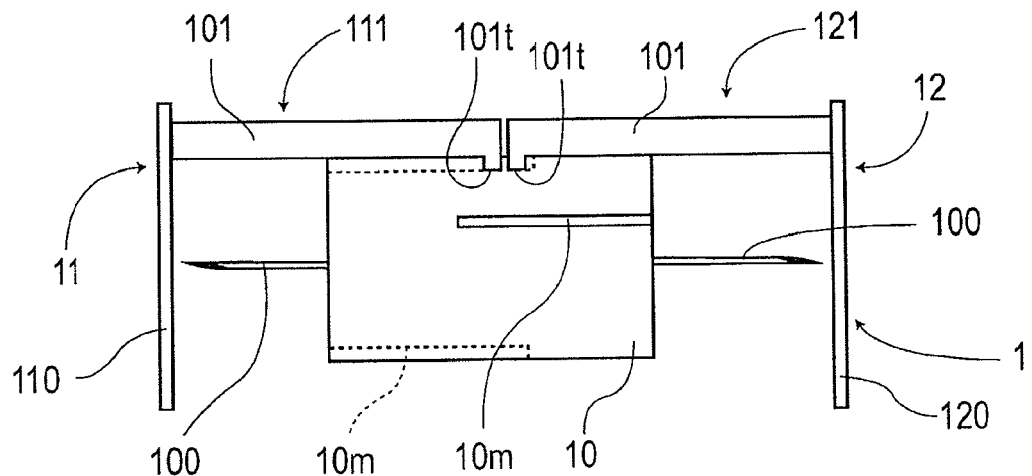
FIG. 5 is a side view of a pair of holder members and a retaining member showing a not axially retractable state in example 1.

As shown in FIGS. 3 to 5, on the inner peripheral surface of the extreme end portion of the pillar-shaped part 101, a convex part 101t projecting toward the inner periphery side is formed. This convex part 101t engages with the guide groove 10m in the retaining member 10, and advances and retreats in the axial direction along the guide groove 10m. In FIGS. 3 to 5, one pillar-shaped part 101 of each of the holder members 11 and 12 is shown for ease of understanding.

Figure 6:
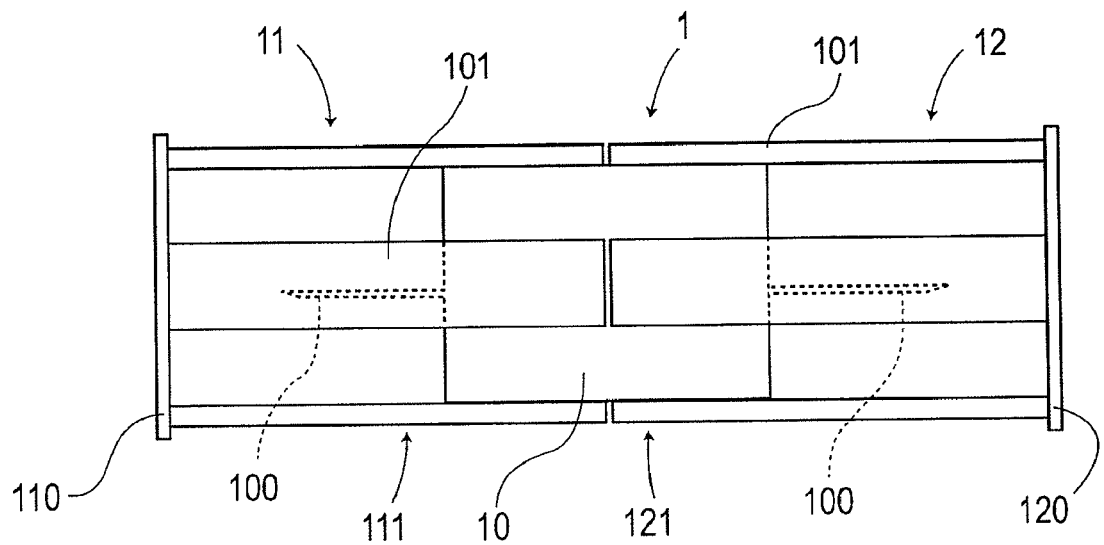
FIG. 6 is a side view of an injection needle cartridge in a state of not axially retractable in example 1.
Figure 7:
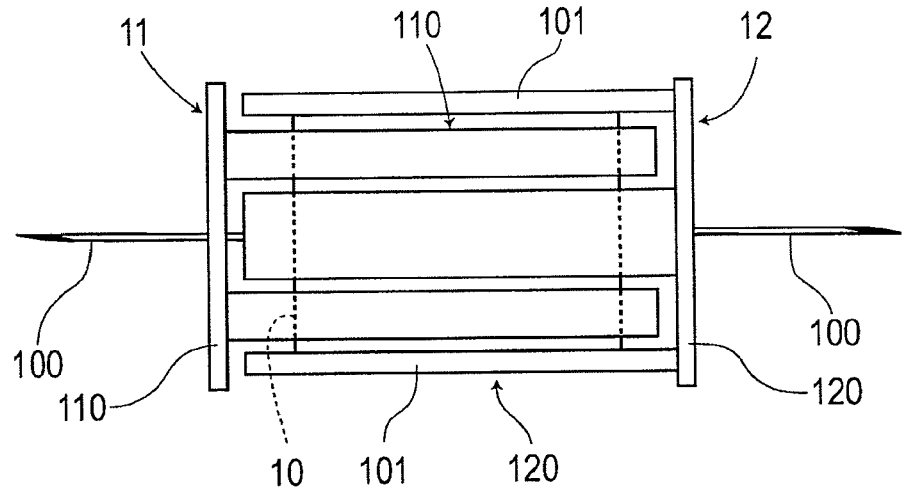
FIG. 7 is a side view of an injection needle cartridge in a state in which an injection needle is projected in example 1.

In the state in which the convex parts 101t of the slider sections 111 and 121 are positioned in different guide grooves 10m as shown in FIGS. 3 and 4, the pillar-shaped part 101 of one slider section 111 and the pillar-shaped part 101 of the other slider section 121 are in a state of adjoining each other via a radial boundary line, that is, in a state of capable of forming a so-called comb tooth form (refer to FIG. 7). On the other hand, in the state in which the convex parts 101t of the slider sections 111 and 121 are positioned in a common guide groove 10m as shown in FIG. 5, the pillar-shaped part 101 of one slider section 111 and the pillar-shaped part 101 of the other slider section 121 are in a state of being opposed to each other (refer to FIG. 6).

Figure 8:
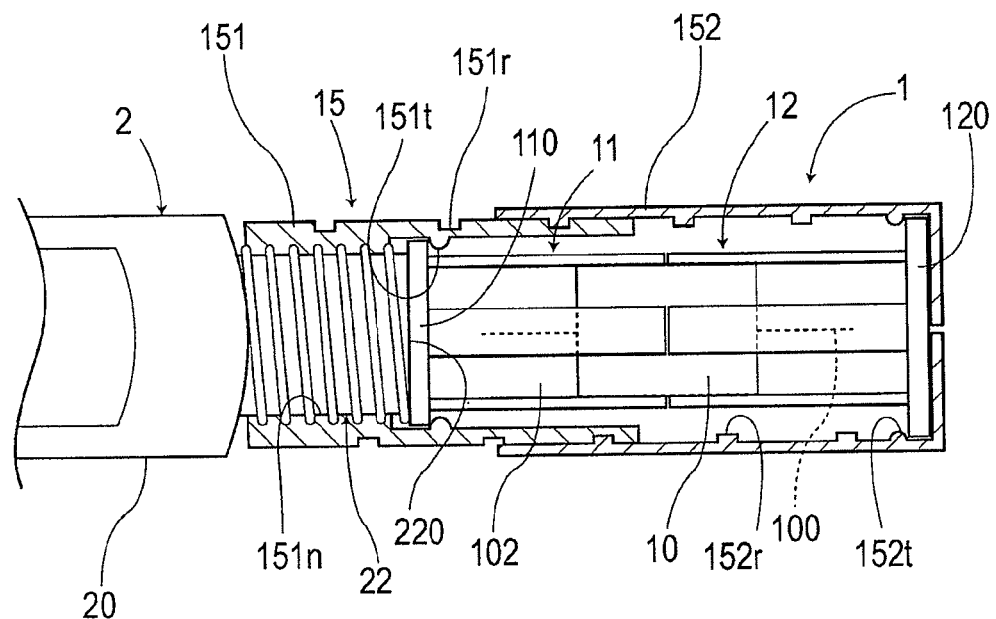
FIG. 8 is a sectional view showing a first mounting construction of an injection needle cartridge with respect to a medication pen in example 1.
Figure 9:
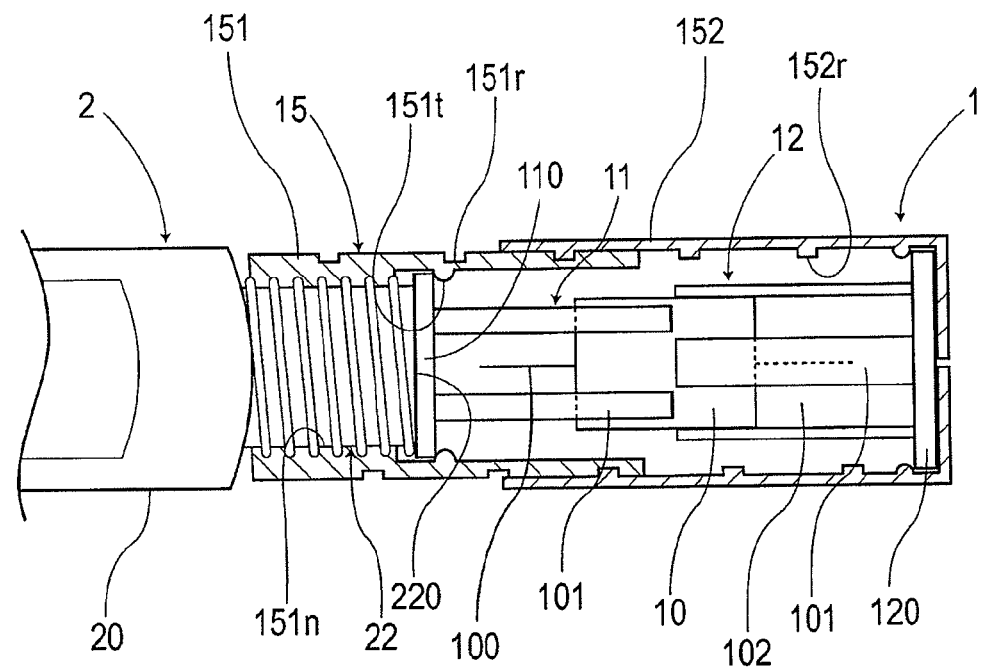
FIG. 9 is a sectional view showing a second mounting construction of an injection needle cartridge with respect to a medication pen in example 1.
Figure 10:
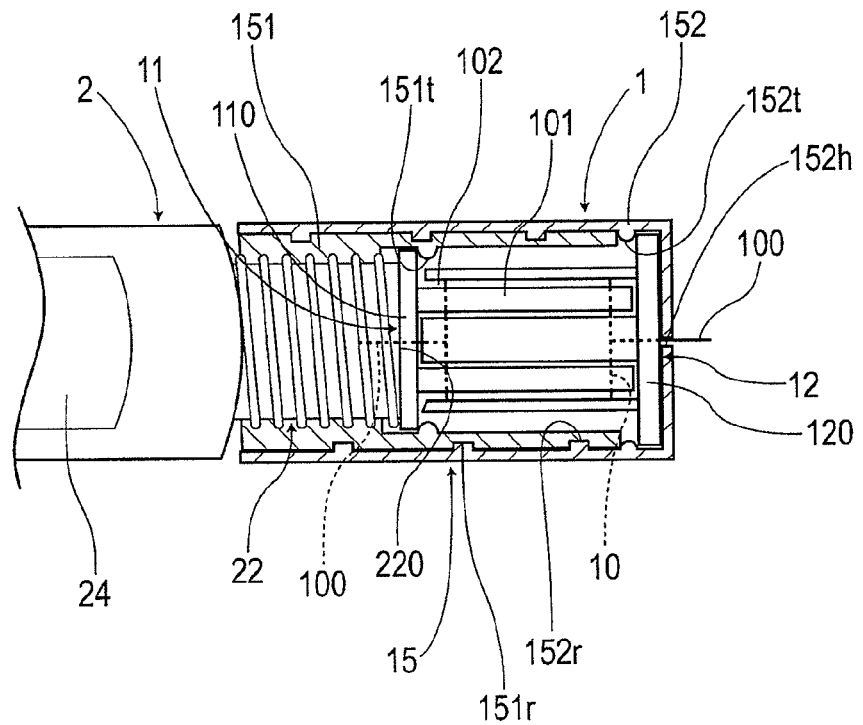
FIG. 10 is a sectional view showing a third mounting construction of an injection needle cartridge with respect to a medication pen in example 1.

Furthermore, as shown in FIGS. 8 to 10, the injection needle cartridge 1 has an applicator 15 for integrally holding the retaining member 10 and the pair of holder members 11 and 12. The applicator 15 includes a substantially cylindrical first member 151 provided with inner peripheral threads 151n engaging with the threaded part 22 at the extreme end outer periphery of the medication pen 2, and a second member 152 advancing and retreating in the axial direction in the state in which the first member 151 is inserted therein. In place of the first member 151 and the second member 152 formed of polypropylene, the members 151 and 152 formed of a resin material such as polyethylene, polyurethane, or polyethylene terephthalate can be used.

As shown in FIGS. 8 and 9, the applicator 15 can turn the pair of holder members 11 and 12 relatively by turning the second member 152 relative to the first member 151. Also, by the advance and retreat of the second member 152 with respect to the first member 151, the containing space 102 formed by the pair of holder members 11 and 12 can be extended and retracted in the axial direction.

Specifically, in the outer peripheral surface of the first member 151, a groove-shaped concave part 151r that is spiral with the axial direction being the center is formed. On the other hand, on the inner peripheral surface of the second member 152, a spiral convex part 152r engaging with the concave part 151r of the first member 151 is formed. For this applicator 15, by the engagement of convex part 152r with the concave part 151r, the whole of the applicator 15 can be extended and retracted in the axial direction according to the relative rotation of the first member 151 and the second member 152.

Furthermore, for the applicator 15, as shown in FIGS. 8 to 10, a moderate frictional force is generated between the inner peripheral surface of the second member 152 and the outer peripheral surface of the second holder member 12. Also, for the applicator 15, a rotation stopper for the bottom plate 110 of the holder member 11 is formed on the inner peripheral surface of the first member 151. Therefore, in the injection needle cartridge 1, the second holder member 12 can be turned relative to the first holder member 11 with the relative rotation of the second member 152 with respect to the first member 151.

On the inner peripheral surface of the first member 151, a convex part 151t for preventing the bottom plate 110 of the first holder member 11 from being pulled out in the axial direction is formed. Also, on the inner peripheral surface of the second member 152, a convex part 152t for preventing the bottom plate 120 of the second holder member 12 from being pulled out in the axial direction is formed. Thereby, the pair of holder members 11 and 12 contained in the applicator 15 can be extended in the axial direction according to the axial extension of the applicator 15.

Next, the configuration of the injection needle cartridge 1 before being used is explained.

In the injection needle cartridge 1 before being used, the applicator 15 in which the first member 151 and the second member 152 are combined with each other is in a state of being extended in the axial direction as shown in FIG. 9. In the applicator 15, the pair of holder members 11 and 12 and the retaining member 10 are contained integrally. In the injection needle cartridge 1 before being used, as shown in FIG. 9, the retaining member 10 is contained in the containing space 102 that is a space between the bottom plates 110 and 120 of the opposed paired holder members 11 and 12, and both ends of the injection needle 100 are positioned in the containing space 102.

In the pair of holder members 11 and 12 in the injection needle cartridge 1 before being used, as shown in FIGS. 5 and 6, the convex parts 101t of the slider sections 111 and 121 are positioned in a common guide groove 10m. In this injection needle cartridge 1, the extreme end faces of the pillar-shaped parts 101 of the slider sections 111 and 121 are in a state of facing to each other. Therefore, in this injection needle cartridge 1, even if an axial load is applied to the pair of holder members 11 and 12, the holder members 11 and 12 are not retracted, and therefore there is less possibility of the injection needle 100 projecting to the outside. That is to say, this injection needle cartridge 1 is highly safe because it can prevent a needle stick accident and the like.

Next, a method for using the above-described injection needle cartridge 1 utilizing the medication pen 2 is explained with reference to FIGS. 8 to 10. In administering an injection using the medication pen 2 mounted with the injection needle cartridge 1, first, as shown in FIG. 8, the injection needle cartridge 1 is mounted to the medication pen 2. In the first embodiment, the injection needle cartridge 1 is mounted to the medication pen 2 together with the applicator 15.

As shown in FIG. 8, by turning the applicator 15 relative to the medication pen 2, the threaded part 22 in the front end portion of the medication pen 2 is threadedly engaged with the applicator 15.

Thereafter, by turning the second member 152 relative to the first member 151, the pair of holder members 11 and 12 are turned relative to each other.

At this time, in the injection needle cartridge 1, a moderate frictional force is generated between the inner peripheral surface of the second member 152 and the second holder member 12 as described above. On the other hand, as shown in FIG. 8, the pair of slider sections 111 and 121 do not engage with each other in a comb tooth form, and are in a state of being turnable easily. Therefore, if the second member 152 is turned in the state in which the medication pen 2 is threadedly engaged with the applicator 15 (FIG. 8), the second member 152 can be turned relative to the first member 151, and accordingly the second holder member 12 can be turned with respect to the first holder member 11.

When the second holder member 12 is turned relative to each other, as shown in FIGS. 3, 4 and 9, the convex parts 101*t* of the second holder member 12 can be moved to the guide grooves 10*m* adjoining in the circumferential direction. Thereby, as shown in FIGS. 3 and 4, the convex parts 101*t* of the holder members 11 and 12 are positioned in different guide grooves 10*m*, and as shown in FIG. 9, the pillar-shaped parts 101 of the slider sections 111 and 121 can be arranged in a comb tooth form.

In this injection needle cartridge 1, the pillar-shaped parts 101 are formed so that when the convex parts 101*t* move between the adjacent guide grooves 10*m*, a moderate click feeling caused by elastic deformation of the pillar-shaped parts 101 formed of a resin material can be obtained. By this click feeling, the user can perform the above-described operation with high reliability while checking the operation. Thereby, as shown in FIG. 9, the pair of holder members 11 and 12 can be set in an axially retractable state.

When the second member 152 is turned further based on the state shown in FIG. 9, by the engagement of the spiral convex part 152*r* at the inner periphery of the second member 152 with the spiral concave part 151*r* at the outer periphery of the first member 151, the applicator 15 in which the first member 151 and the second member 152 are combined with each other can be retracted in the axial direction. At the same time, the pair of holder members 11 and 12 in the applicator 15 can be retracted in the axial direction.

When the pair of holder members 11 and 12 are retracted in the axial direction, the containing space 102 therein is retracted in the axial direction. When the axial length of the containing space 102 decreases, as shown in FIG. 10, the injection needle 100 retained by the retaining member 10 penetrates through the through holes 105 (refer to FIG. 1) in the bottom plates 110 and 120, and can project to the outside penetrating the film 13 (refer to FIG. 1). On the medication pen 2 side, the injection needle 100 sticks the membrane 220 of the medication pen 2, and the needle point is positioned within the medicine cartridge 24. On the other hand, on the front end side of the medication pen 2, that is, on the outer side, the injection needle 100 penetrates through a through hole 152*h* in the second member 152 of the applicator 15 and projects toward the outside.

The injection needle cartridge 1 of the first embodiment can be set in an injectable state by the above-described procedure. For the medication pen 2 mounted with the injection needle cartridge 1, after the injection needle 100 on the front end side has been stuck in the human body's skin or the like, the medicine in the medicine cartridge 24 can be injected by pushing in the push rod 21. At this time, in this medication pen 2, by setting the dosage beforehand by using the dosage setting mechanism 23, the medicine of a preset dosage can be injected with high accuracy.

Next, a disposal method for the injection needle cartridge 1 after the finish of injection is explained. In removing the injection needle cartridge 1, first, the second member 152 of the applicator 15 is turned in the reverse direction. By doing this, by the engagement of the spiral convex part 152*r* on the inner peripheral surface of the second member 152 with the spiral concave part 151*r* on the outer peripheral surface of the first member 151, the whole of the applicator 15 can be extended in the axial direction. In the injection needle cartridge 1, the bottom plate 110 of the first holder member 11 engages with the convex part 151*t* of the first member 151, and the bottom plate 120 of the second holder member 12 engages with the convex part 152*t* of the second member 152. Therefore, in this injection needle cartridge 1, as shown in FIG. 9, the pair of holder members 11 and 12 can be extended in the axial direction with the axial extension of the applicator 15.

When the pair of holder members 11 and 12 are extended in the axial direction as shown in FIG. 9, the axial length of the containing space 102 can be increased, so that the injection needle 100 can be withdrawn from the through holes 105 (FIG. 1) in the bottom plates 110 and 120. On the medication pen 2 side, the injection needle 100 is withdrawn from the membrane 220, and the needle point is positioned in the containing space 102 in the pair of holder members 11 and 12. On the other hand, on the front end side of the medication pen 2, that is, on the outer side, the injection needle 100 is withdrawn from the through hole 105 in the bottom plate 120, and the needle point is positioned in the containing space 102 in the pair of holder members 11 and 12.

Thereafter, as shown in FIGS. 3 and 9, the second member is turned further so that the pair of holding members 11 and 12 are extended until the convex parts 101*t* of the holder members 11 and 12 are positioned in the end portions of the guide grooves 10*m*. Thus, the pillar-shaped parts 101 of the slider sections 111 and 121 form a state of not overlapping each other in the axial direction. That is to say, for the pair of holder members 11 and 12, the state in which the slider sections 111 and 121 are engaged with each other in a comb tooth form is dissolved, and the state in which the slider sections 111 and 121 can easily be turned relative to each other about the axis of the retaining member 10 is formed. Since the guide groove 10*m* in the retaining member 10 is formed with the end portion, there is less possibility that the holder members 11 and 12 come off the retaining member 10 when the pair of holder members 11 and 12 are extended in the axial direction.

As described above, a moderate frictional force is generated between the second member 152 and the holder member 12. Therefore, when the second member 152 is turned further in the state in which the pair of holder members 11 and 12 can easily be turned relative to each other as described above, the holder member 12 can be turned following the second member 152. With respect to the other holder member 11, the holder member 12 can be turned relatively. When the second holder member 12 is turned relative to the first holder member 11, as shown in FIGS. 5 and 8, the convex parts 101*t* of the second holder member 12 are moved to the guide grooves 10*m* adjoining in the circumferential direction, and the convex parts 101*t* of the holder members can be positioned in a common guide groove 10*m*. Thereby, as shown in FIG. 8, the extreme end faces of the pillar-shaped parts 101 of the pair of holder members 11 and 12 can be caused to face to each other, and the state in which the pair of holder members 11 and 12 are not axially retractable can be formed.

Thereafter, by turning the whole of the applicator 15 with respect to the medication pen 2, the injection needle cartridge 1 and the applicator 15 can be removed from the medication pen 2. In the injection needle cartridge 1 having been removed as described above, the pair of holder members 11 and 12 are extended in the axial direction, and are in a state of being not retractable. That is to say, in this injection needle cartridge 1, the extreme ends of the injection needle 100 are contained in the holder members 11 and 12, and even if an axial load is applied, the possibility of the injection needle 100 projecting again is very little. Therefore, in the disposal of the used injection needle cartridge 1, the possibility of the occurrence of a needle stick accident is very little.

The above is an explanation of the details of the first embodiment.

Next, the second embodiment is explained. In this embodiment, based on the medication pen of the first embodiment, a cap-shaped cap section 16 is used in place of the applicator. The details of this embodiment are explained with reference to FIGS. 11 to 14.

Figure 11:
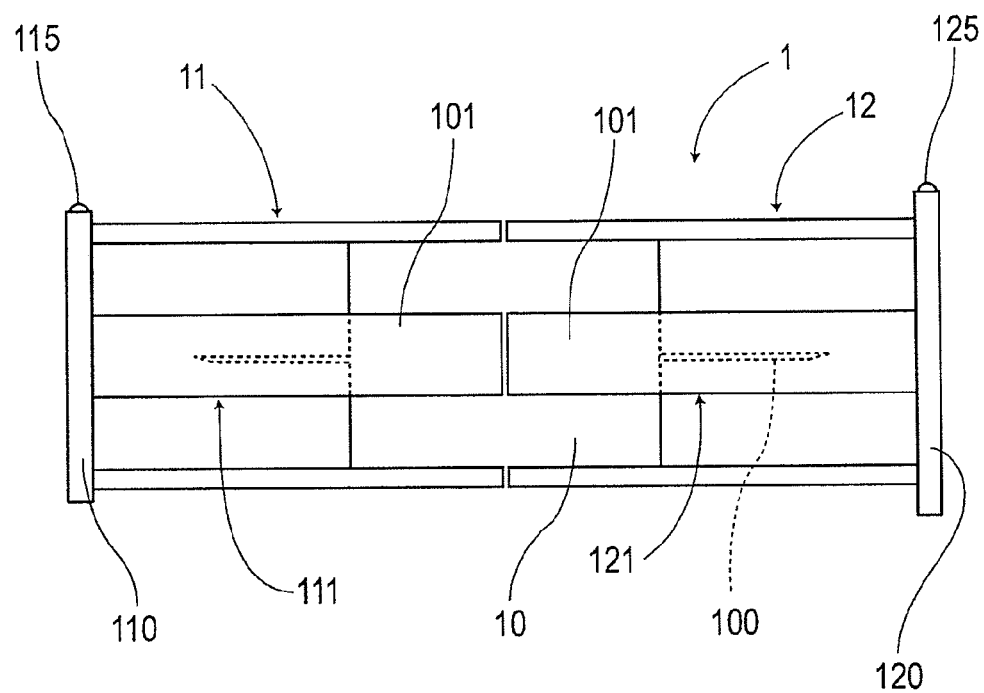
FIG. 11 is a side view of an injection needle cartridge in example 1.

As shown in FIG. 11, the injection needle cartridge 1 is configured, so that based on the injection needle cartridge of the first embodiment, a convex part 115, 125 projecting toward the outer periphery side is provided at one place at the outer periphery of the bottom plate 110, 120 of the holder member 11, 12.

Figure 12:
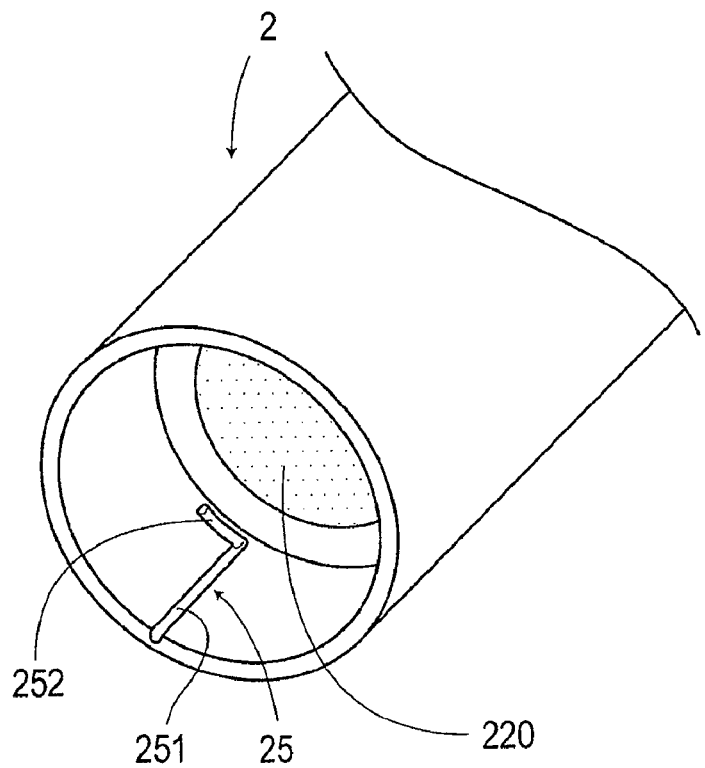
FIG. 12 is a perspective view of the front end portion of a medication pen in example 1.

On the other hand, as shown in FIG. 12, the medication pen 2 of the second embodiment is configured so that based on the medication pen of the first embodiment, the barrel forming the outer periphery side of the membrane 220 is extended in the axial direction, and a groove-shaped concave part 25 for receiving the convex part 115 of the first holder member 11 is provided at the inner periphery of the substantially cylindrical extending part. The concave part 25 is formed by combining a first concave part 251 extendingly provided in the axial direction with a second concave part 252 extendingly provided in the circumferential direction from the end portion on the membrane 220 side of the first concave part 251.

Figure 13:
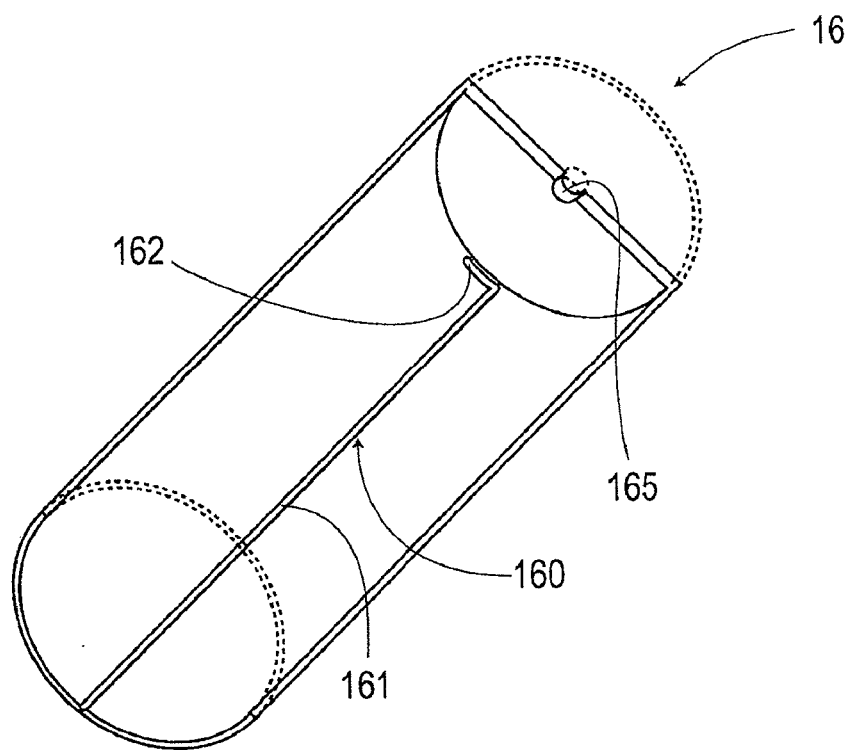
FIG. 13 is a partially sectional view of a cap in example 1.

As shown in FIG. 13, the cap section 16 is a bottomed substantially cylindrical member that is formed of polypropylene and has an opening end on one side. In the bottom portion thereof, a through hole 165 for allowing the injection needle 100 to penetrate through and project is formed. In the inner peripheral surface of the cap section 16, a concave part 160 for receiving the convex part 125 of the second holder member 12 is formed. The concave part 160 is formed by combining a first concave part 161 extendingly provided in the axial direction with a second concave part 162 extendingly provided in the circumferential direction from the end portion on the bottom side of the first concave part 161.

Next, a method for using this medication pen 2 is explained. In administering an injection by using the medication pen 2, first, as shown in FIGS. 11 and 13, the injection needle cartridge 1 is put in the cap section 16. At this time, the convex part 125 on the injection needle cartridge 1 side is engaged with the concave part 160 in the cap section 16.

Next, the front end of the medication pen 2, which is a body part, is inserted into the cap section 16 containing the injection needle cartridge 1. In the second embodiment, an alignment mark (not shown) is printed at one place in the circumferential direction at the outer periphery of each of the cap section 16 and the medication pen 2 so that the circumferential position of the convex part 115 on the injection needle cartridge 1 side contained in the cap section 16 coincides with the circumferential position of the concave part 25 on the medication pen 2 side as shown in FIGS. 11 to 13. Therefore, for the medication pen 2 of the second embodiment, the convex part 115 of the injection needle cartridge 1 can be engaged with the concave part 25 of the medication pen 2 with high reliability by inserting the medication pen 2 in the state in which the circumferential positions of the alignment marks are substantially caused to coincide with each other.

When the medication pen 2 is inserted most deeply in the cap section 16, as shown in FIGS. 11 to 13, the convex part 115 of the injection needle cartridge 1 is positioned in the second concave part 252, and the convex part 125 thereof is positioned in the second concave part 162. When the cap section 16 and the medication pen 2 are turned relative to each other in this state, the convex parts 115 and 125 of the injection needle cartridge 1 move in the direction such as to separate from the first concave part 251 or 161, and can reach the end portions of the second concave parts 252 and 162.

When the cap section 16 and the medication pen 2 are turned relative to each other further in this state, this turning operation can be transmitted to the injection needle cartridge 1, so that the pair of holder members 11 and 12 can be turned relative to each other. Thus, the state in which the extreme end faces of the pillar-shaped parts 101 of the holder members 11 and 12 face to each other (refer to FIG. 6) can be changed to the retractable state in which the pillar-shaped parts of the holder members 11 and 12 are alternately displaced in a comb tooth form.

After this retractable state has been formed, the front end of the cap section 16 is pressed against an injection portion, by which the medication pen 2 can be inserted further in the cap section 16, and accordingly the injection needle cartridge 1 can be retracted in the axial direction. Thereby, one end portion of the injection needle 100 can be pierced into the membrane 220 of the medication pen 2, and the other end portion thereof can be projected to the outside from the cap section 16. Thereafter, by pushing in the push rod of the medication pen 2, as in the first embodiment, a prescribed amount of medicine can be injected.

Next, a disposal method for the used injection needle cartridge 1 is explained. First, the cap section is withdrawn from the medication pen 2. At this time, as described above with reference to FIGS. 11 to 13, the convex parts 115 and 125 of the holder members 11 and are engaged with the second concave parts 162 and 252 of the cap section 16 and the medication pen 2. Therefore, the axial length of the pair of holder members 11 and 12 can be increased according to the withdrawal of the cap section 16. Thereby, the injection needle 100 can be accommodated in the pair of holder members 11 and 12.

When the medication pen 2 is turned in the reverse direction with respect to the cap section 16 in the state in which the pair of holder members 11 and 12 extend fully in the axial direction, accordingly, the convex parts 115 and 125 of the injection needle cartridge 1 move to the other end of the second concave part 252 or 162, that is, to the end portions on the first concave part 251, 161 side. When the medication pen 2 is turned further in this state, the pair of holder members 11 and 12 can be turned relative to each other in association with the relative rotation of the cap section 16 and the medication pen 2. Thereby, the state in which the extreme end faces of the pillar-shaped parts 101 of the slider sections 111 and 121 of the holder members 11 and 12 face to each other (refer to FIG. 6) can be formed.

Thereafter, the cap section 16 is pulled completely out of the medication pen 2, and the injection needle cartridge 1 is removed from the interior of the cap section 16, by which the used injection needle cartridge 1 can be disposed of. The injection needle cartridge 1 removed from the cap section 16 is in the state in which the extreme end faces of the pillar-shaped parts 101 of the slider sections 111 and 121 face to each other (refer to FIG. 6). That is to say, the used injection needle cartridge 1 is in the state in which the injection needle 100 is contained in the containing space 102, and the containing space 102 is not axially retractable.

The above is an explanation of the details of the second embodiment.

Next, the third embodiment is explained. In the third embodiment, based on the medication pen of the second embodiment, the external shape of the injection needle cartridge 1 is changed, and also the configuration of a cap section 17 is changed. The details thereof are explained with reference to FIGS. 15 to 17.

The medication pen 2 of the third embodiment is integrally assembled to the cap section 17 via a joint 18 serving as a connecting member. For the injection needle cartridge 1, the bottom plate 110, 120 (refer to FIG. 1) of the holder member 11, 12 has a hexagonal shape.

Figure 15:
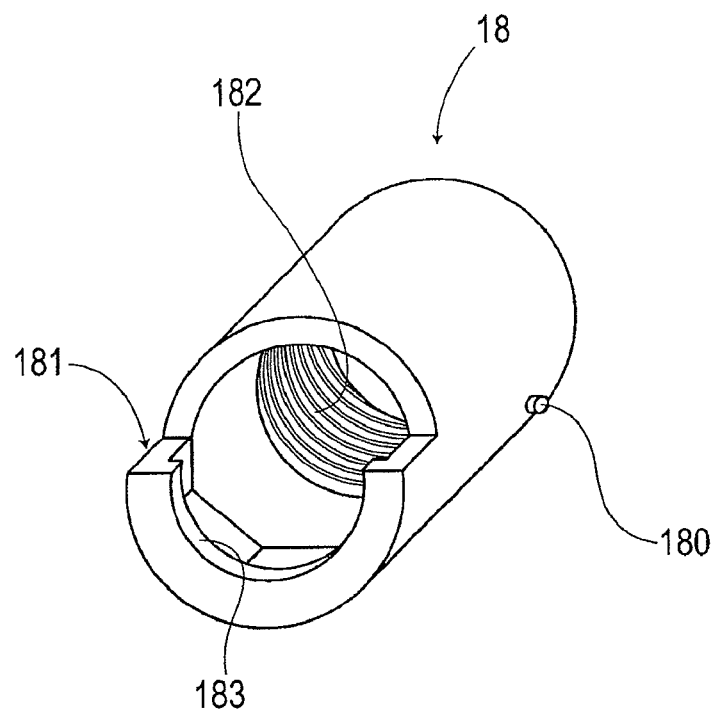
FIG. 15 is a perspective view of a joint in example 1.

As shown in FIG. 15, the joint 18 is a substantially cylindrical part formed of polypropylene. On the inner peripheral surface thereof corresponding to the medication pen 2 side, an inner peripheral threaded part 182 engaging with the threaded part (symbol 22 in FIG. 2) at the outer periphery at the front end of the medication pen 2 is formed. On the other hand, in the end portion on the opposite side, a notch having a substantially semicircular cross section is formed, and thereby a semicircular part 181 is formed. Further, on the outer peripheral surface of the joint 18, a convex part 180 for restricting the relative motion of the cap section 17 with respect to the medication pen 2 is formed.

Figure 14:
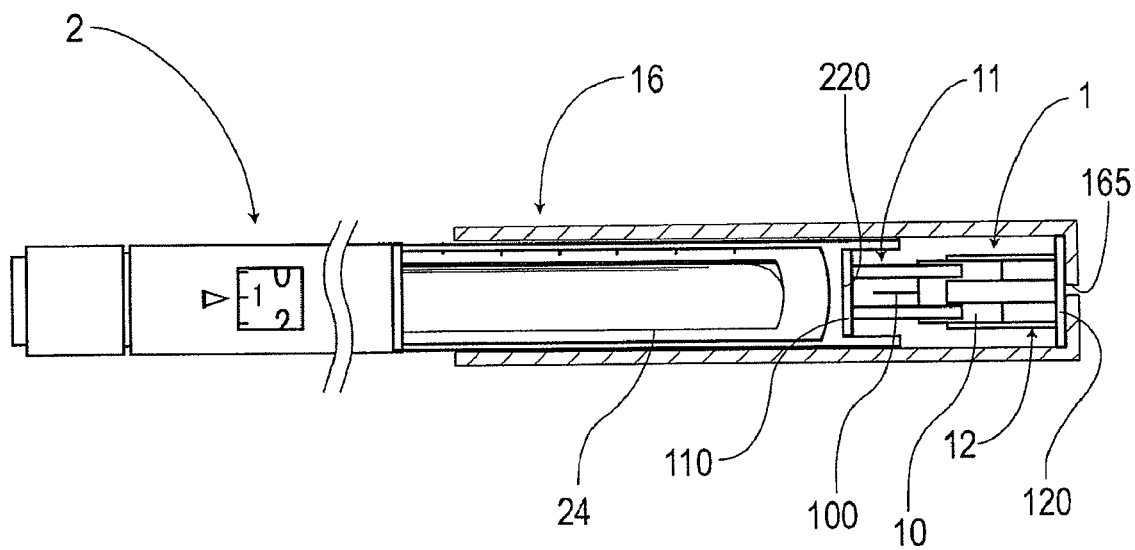
FIG. 14 is a sectional view showing a mounting construction of an injection needle cartridge with respect to a medication pen in example 1.

In the semicircular part 181 of the joint 18, an inner periphery shape corresponding to the hexagonal shape of the bottom plate 110 is formed to restrict the rotation of the holder member (symbol 11 in FIG. 14). Further, in the end portion of the semicircular part 181, a locking part 183 for restricting the axial displacement of the bottom plate 110 is provided.

Figure 16:
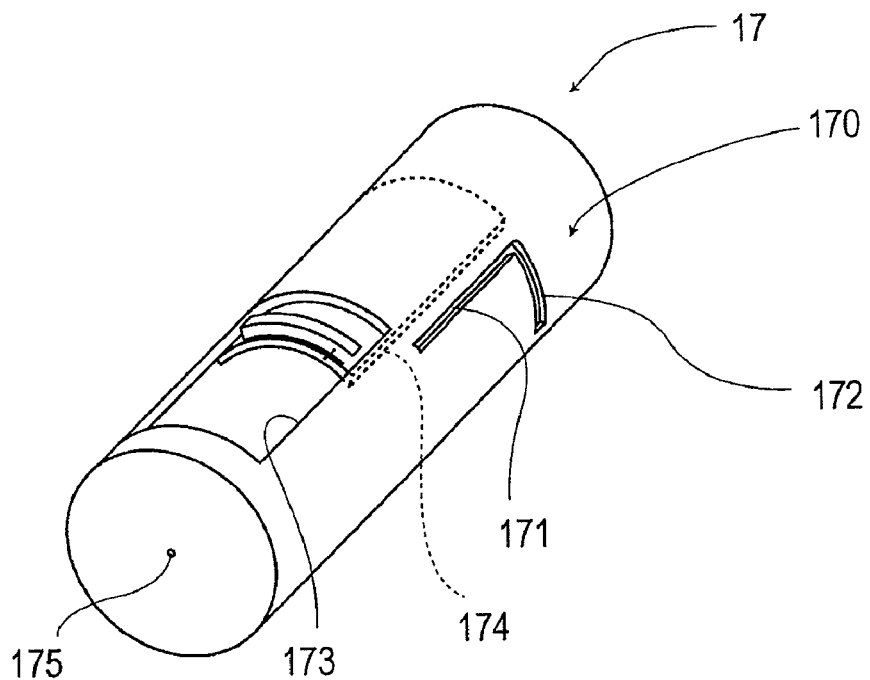
FIG. 16 is a perspective view of a cap in example 1.

As shown in FIG. 16, the cap section 17 is a bottomed substantially cylindrical member having an opening end in one end portion thereof, and has a through hole 175 for allowing the injection needle to penetrate through in the bottom portion thereof. The cap section has an opening window 173 with a movable shutter 174 for putting in and taking out the injection needle cartridge (symbol 1 in FIG. 14). Further, the cap section 17 has a through groove shaped slit 170 for receiving the convex part 180 of the joint 18.

As shown in FIGS. 15 and 16, the slit 170 is formed by combining an advance/retreat slit part 171 provided along the axial direction with a rotation slit part 172 extendingly provided along the circumferential direction from the end portion corresponding to the medication pen 2 side of the advance/retreat slit part 171. The cap section 17 in the state in which the convex part 180 engages with the advance/retreat slit part 171 can be advanced and retreated in the axial direction with respect to the medication pen 2. On the other hand, the cap section 17 in the state in which the convex part 180 engages with the rotation slit part 172 can be turned relative to the medication pen 2.

As shown in FIG. 16, the opening window 173 of the cap section 17 is an opening part formed so as to be capable of containing the injection needle cartridge in a state of extending in the axial direction. On the inside of the cap section 17, a locking part (not shown) is formed to restrict the rotation and axial position of the holder member (symbol 12 in FIG. 14) positioned on the bottom side. The movable shutter 174 is formed by a plate having a substantially arcuate cross section that can advance and retreat in the axial direction, and can open and close the opening window 173 by means of the axial advance and retreat thereof.

Figure 17:
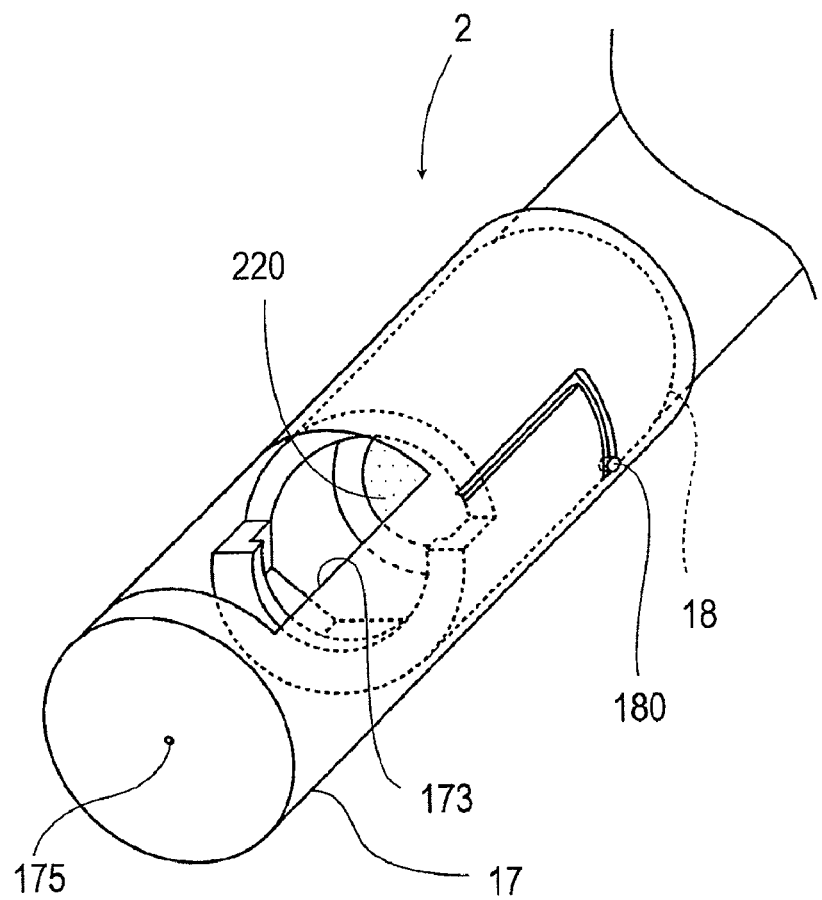
FIG. 17 is a perspective view showing an assembling construction of a cap with respect to a medication pen in example 1.

As shown in FIGS. 15 to 17, the medication pen 2 threadedly connects the joint 18 to the front end thereof, and also assembles the cap section 17 so that the convex part 180 of the joint 18 engages with the slit 170. In administering an injection by using this medication pen 2, first, the opening window 173 is opened by retreating the movable shutter 174 in the axial direction.

Then, the injection needle cartridge is put into the cap section 17 through the opening window 173. At this time, one holder member 11 is engaged with the locking part 183 of the joint 18, and the other holder member 12 is engaged with a locking part (not shown) of the cap section 17. Thereby, the configuration can be made such that the pair of holder members 11 and 12 can be turned relative to each other according to the relative rotation of the cap section 17 with respect to the medication pen 2, and also the pair of holder members 11 and 12 can be advanced and retreated in the axial direction according to the axial advance and retreat of the cap section 17.

After the injection needle cartridge has been put into the cap section 17 as described above, and the movable shutter 174 has been closed, the cap section 17 is turned relative to the medication pen 2. At this time, the convex part 180 of the joint 18 moves in the rotation slit part 172. At the same time, the pair of holder members 11 and 12 can be turned relative to each other with the relative rotation of the cap section 17 and the joint 18. Thus, the state in which the extreme end faces of the pillar-shaped parts of the slider sections face to each other (refer to FIG. 6) can be changed to the retractable state in which the pillar-shaped parts 101 are alternately displaced in a comb tooth form (refer to FIG. 7).

Thereafter, by pushing the cap section 17 against the medication pen 2, the convex part 180 of the joint 18 is moved in the advance/retreat slit part 171, and accordingly the axial distance of the pair of holder members 11 and 12 can be shortened. Thereby, the injection needle can be projected from the through hole of the cap section 17.

Subsequently, in disposing of the used injection needle cartridge, first, the cap section 17 is withdrawn from the medication pen 2 so that the convex part 180 of the joint 18 reaches the rotation slit part 172. Thereby, the axial distance of the pair of holder members 11 and 12 can be increased, and accordingly the injection needle can be accommodated in the pair of holder members 11 and 12.

Furthermore, when the cap section 17 is turned in the reverse direction relative to the medication pen 2, the pair of holder members 11 and 12 can be turned relative to each other. Thereby, the state in which the extreme end faces of the pillar-shaped parts of the slider sections face to each other (refer to FIG. 6) can be formed. Thereafter, the movable shutter 174 is retreated in the axial direction to open the opening window 173, and the used injection needle cartridge is taken out. The taken-out injection needle cartridge can be handled with high safety because the injection needle is contained in the containing space 102, and the containing space 102 is not axially retractable.

The above is an explanation of the details of the third embodiment.

In the embodiment of this example, based on the above-described third embodiment, the inner ring 31 constituting the rotation restricting mechanism for restricting the relative rotation of the paired holder members 11 and 12 is added to the retaining member 10. Further, in this example, based on the medication pen of the third embodiment, the configurations of the injection needle cartridge 1, the joint 18, the cap section 17, and the like are changed. The details of this example are explained with reference to FIGS. 18 to 26.

Figure 18:
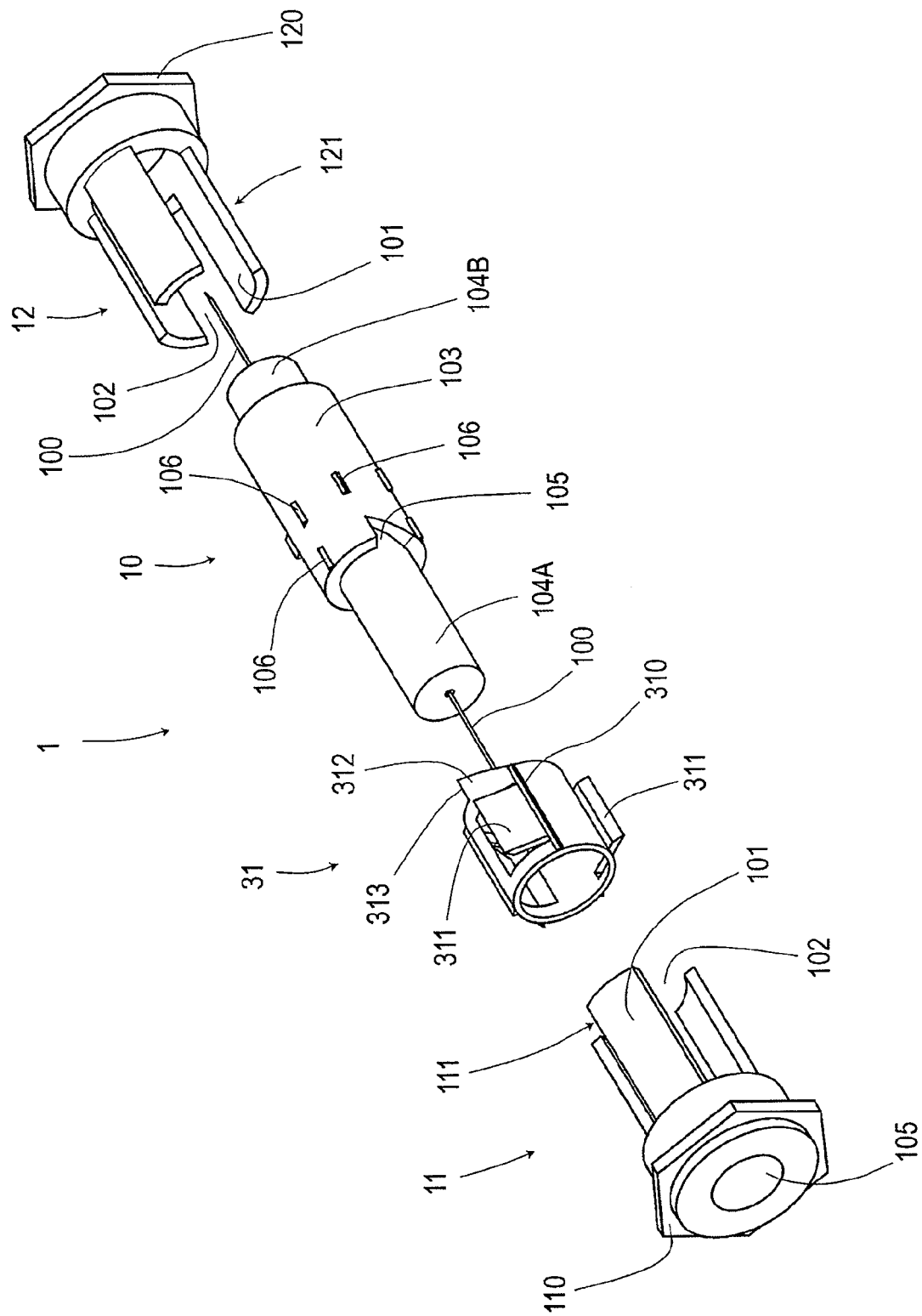
FIG. 18 is an exploded assembly view showing an assembling construction of an injection needle cartridge in example 1.
Figure 19:
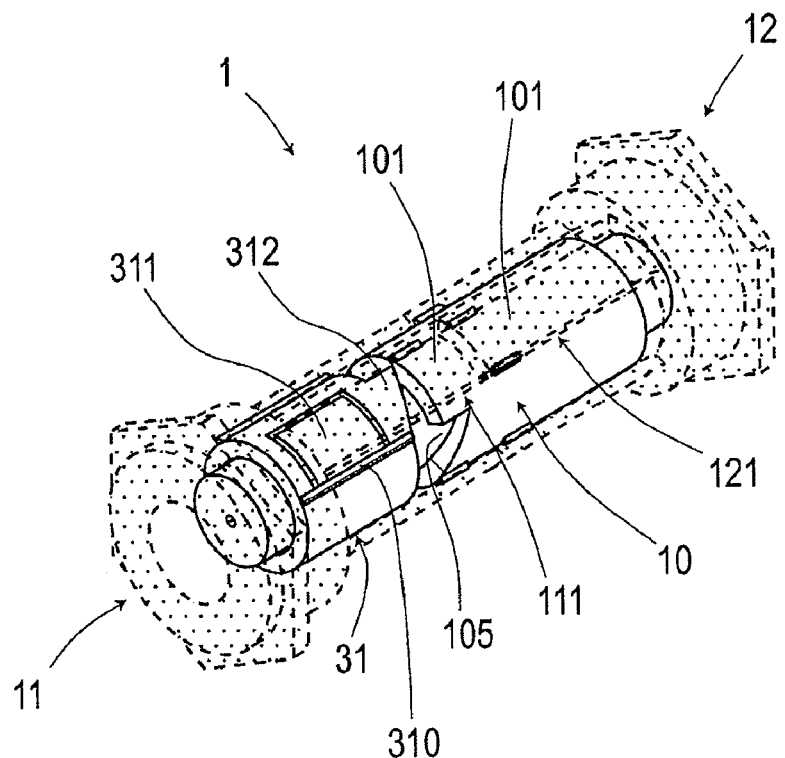
FIG. 19 is a perspective view of an unused injection needle cartridge in example 1.

As shown in FIGS. 18 and 19, the injection needle cartridge 1 of this example includes the substantially columnar retaining member 10 through which the injection needle 100 penetrates in the axial direction, the first holder member 11 including the first slider section 111 consisting of the pillar-shaped parts 101 provided at three places in the circumferential direction, and the second holder member 12 including the second slider section 121 consisting of the pillar-shaped parts 101 provided at three places in the circumferential direction.

In particular, the retaining member 10 of the injection needle cartridge 1 of this example includes the inner ring 31 placed around the retaining member 10. FIG. 18 is an exploded assembly view in which parts are shown by being separated in the axial direction.

As shown in FIGS. 18 and 19, the holder member 11, 12 has the hexagonal bottom plate 110, 120, and the slider sections 111, 121 including the pillar-shaped parts 101 erected from the bottom plate 110, 120 at intervals of 120 degrees. The formation width of each of the pillar-shaped parts 101 is 60 degrees in the circumferential direction. The bottom plate 110, 120 is formed with the through hole 105 for allowing a small-diameter part 104 of the retaining member 10 to penetrate through and project. Although the bottom plate 110, 120 of this example has a shape such that a column penetrates a hexagonal plate, the functional configuration is the same as that of the bottom plate of the injection needle cartridge 1 of the third embodiment.

As shown in FIGS. 18 and 19, the inner ring 31 is a substantially cylindrical member formed of polypropylene. The inner ring 31 is provided with three substantially rectangular engagement pieces 311 that are formed by cutting the outer peripheral wall surface of the inner ring 31 into a U shape and are arranged at three places at intervals of 120 degrees. Each of the engagement pieces 311 is connected to the body side of the inner ring 31 via only one side that is substantially parallel with the axial direction and is positioned on the same side in the circumferential direction. The engagement pieces 311, each of which is a part of the inner ring 31 formed of polypropylene and having elasticity, is in a state of being opened to the outside in the radial direction as shown in FIG. 18 in the state in which no external force is applied.

Furthermore, as shown in FIGS. 18 and 19, the inner ring 31 has a detent 310, which is a ridge-shaped convex part extendingly provided along the axial direction, on the outer peripheral surface thereof corresponding to the root portion of each of the engagement pieces 311. Further, the inner ring 31 has an engagement convex part 312, which projects axially, on the end face thereof positioned on the side of direction in which the retaining member 10 is inserted. In the engagement convex part 312, the projection amount thereof increases gradually toward the circumferential direction from the root side to the extreme end side of the engagement piece 311, and an engagement face 313 substantially parallel with the axial direction is provided at a position at which the projection amount is at the maximum. The axial projection amount of the engagement convex part 312 changes suddenly from the maximum projection amount to zero via the engagement face 313 parallel with the axial direction.

As shown in FIGS. 18 and 19, the retaining member 10 is a substantially columnar member that is formed with a large-diameter part 103 provided at a middle position in the axial direction in an offset manner, and provided with the small-diameter parts 104 at both ends in the axial direction. The small-diameter parts 104 are formed so that the axial length of one small-diameter part 104A is longer than that of the other small-diameter part 104B. The small-diameter part 104A having a longer axial length is configured so that the inner ring 31 is placed around, and when the inner ring 31 is placed around, the small-diameter part 104A can still project in the axial direction. The inner ring 31 can advance and retreat in the axial direction and can turn in the circumferential direction in a state of being placed around the small-diameter part 104A. The inner ring 31 placed around the small-diameter part 104A is formed so as to be integral with the large-diameter part 103 when the engagement pieces 311 are retracted toward the inside in the radial direction.

As shown in FIGS. 18 and 19, the large-diameter part 103 has ridge-shaped convex parts 106, which restrict the circumferential relative rotation of the slider sections 111 and 121, on the outer surface thereof. The convex parts 106 include ones that engage with the pillar-shaped parts 101 of the first slider section 111 and ones that engage with the pillar-shaped parts 101 of the second slider section 121. The convex parts 106 for restricting the relative rotation of the first slider section 111 are positioned at three places in the circumferential direction at intervals of 120 degrees. The convex parts 106 for restricting the relative rotation of the second slider section 121 are positioned at six places in the circumferential direction at intervals of 60 degrees. By the three convex parts 106 for the first slider section 111, the rotation of the first slider section 111 can be restricted within 60 degrees, in which range the first slider section 111 consisting of the pillar-shaped parts 101 having a formation width of 60 degrees in the circumferential direction can be turned. Also, by the six convex parts 106 for the second slider section 121, the rotation of the second slider section 121 consisting of the same pillar-shaped parts 101 can be restricted.

Furthermore, as shown in FIGS. 18 and 19, on the end surface forming a level difference between the large-diameter part 103 and the small-diameter part 104A, that is, on the end surface on the inner ring 31 side, a concave-shaped engagement concave part 105 depressing in the axial direction is formed so as to snugly fit to the engagement convex part 312 of the inner ring 31. In the state in which the engagement convex part 312 of the inner ring 31 and the engagement concave part 105 of the retaining member 10 engage with each other, the relative rotation in the direction such that the projection amount of the engagement convex part 312 increases can be restricted with high reliability by the action of the engagement face 313 of the inner ring 31.

In the assembled (unused) injection needle cartridge 1, as shown in FIGS. 18 and 19, the retaining member 10 around which the inner ring 31 is placed is contained in a containing space 102 formed by the pair of holder members 11 and 12. In this injection needle cartridge 1, the engagement pieces 311 of the inner ring 31 are positioned on the inner periphery side of the pillar-shaped parts 101 of the first slider section 111. The engagement pieces 311 are elastically deformed by an external force in the inner periphery direction applied by the pillar-shaped parts 101.

Furthermore, the assembled (unused) injection needle cartridge 1 is in the state in which the engagement convex part 312 of the inner ring 31 and the engagement concave part 105 of the retaining member 10 do not engage with each other as shown in FIGS. 18 and 19. The injection needle cartridge 1 in this state is in the state in which the inner ring 31 retreats in the axial direction, and also the inner ring 31 is turned through 60 degrees counterclockwise as viewed from the left lower side in FIG. 19 with the rotation position at which the circumferential position of the engagement concave part 105 and the circumferential position of the engagement convex part 312 substantially coincide with each other being the reference. In this state, the slider sections 111 and 121 of the pair of holder members 11 and 12 face to each other so that they are not retractable in the axial direction.

Figure 20:
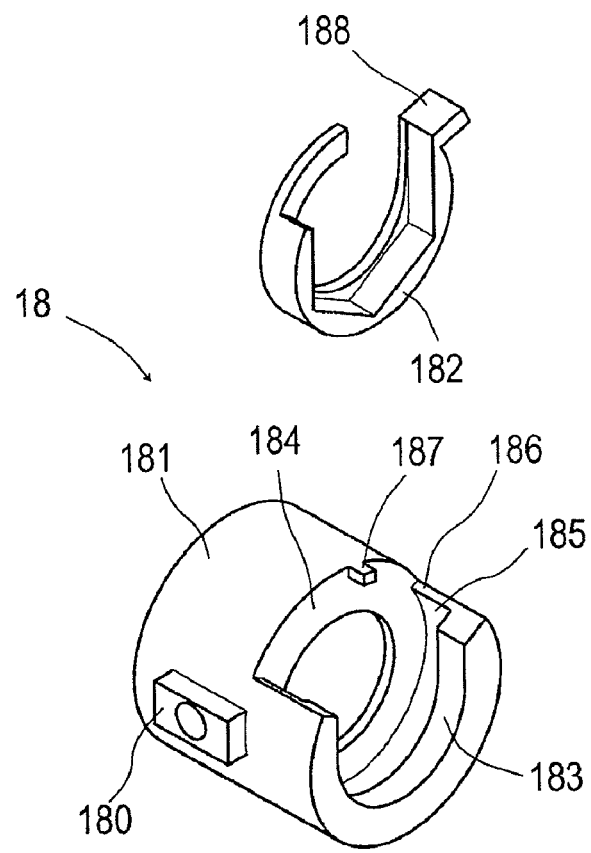
FIG. 20 is an exploded assembly view of a joint in example 1.

As shown in FIG. 20, the joint 18 of this example is a part formed by combining a rotation member 182 and a joint body part 181, wherein the rotation member 182 is a member substantially of an incomplete ring shape in which a part in the circumferential direction is cut away, and has an incomplete hexagonal inner periphery shape in the cross-section, the entire rotation member 182 being in a substantially C-shape, and the joint body part 181 is a member for holding the rotation member 182 in a turnable state. The rotation member 182 is a substantially C-shaped part provided with a cut-away portion at one place in the circumferential direction, and has a rotation lever 188, which projects to the outer periphery side in the radial direction, in the end portion facing to the cut-away portion.

The joint body part 181 is a substantially cylindrical part provided with a partition plate 184 in the middle thereof in the axial direction and also provided with a convex part 180 on the outer peripheral surface thereof. One end part partitioned by the partition plate 184 is a part in which the medication pen 2 that is the same as that of the third embodiment is inserted. The other end part has an incomplete cylindrical shape provided with an opening part close to 120 degrees at one place in the circumferential direction. In the other end part, a holding part 185 is formed facing to the partition plate 184, and also a locking part 183 having a diameter smaller than that of the holding part 185 is provided on the extreme end side. The holding part 185 is a part for holding the rotation member 182 in a turnable state. In assembling, the substantially C-shaped rotation member 182 is put into the holding part 185 while being deflected by elastic deformation. The rotation member 182 held in the holding part 185 can turn in the rotation range between the rotation position at which an edge part 186 of the holding part 185 interferes with the rotation lever 188 and the rotation position at which a convex rotation stopper 187 provided on the partition plate 184 so as to project axially interferes with the rotation lever 188.

Figure 21:
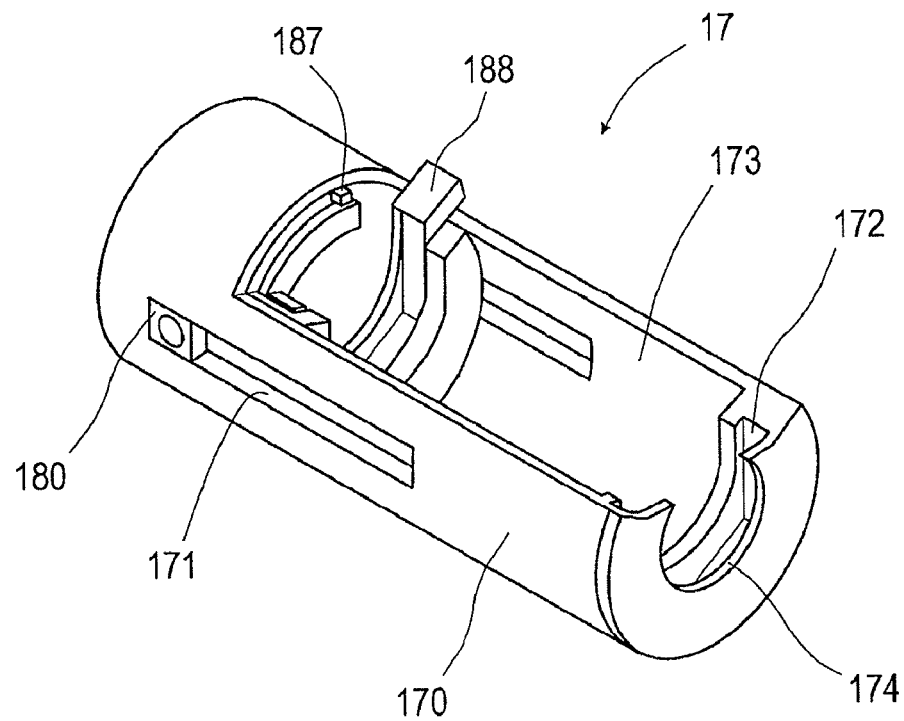
FIG. 21 is a first perspective view of a cap to which a joint is assembled in example 1.
Figure 22:
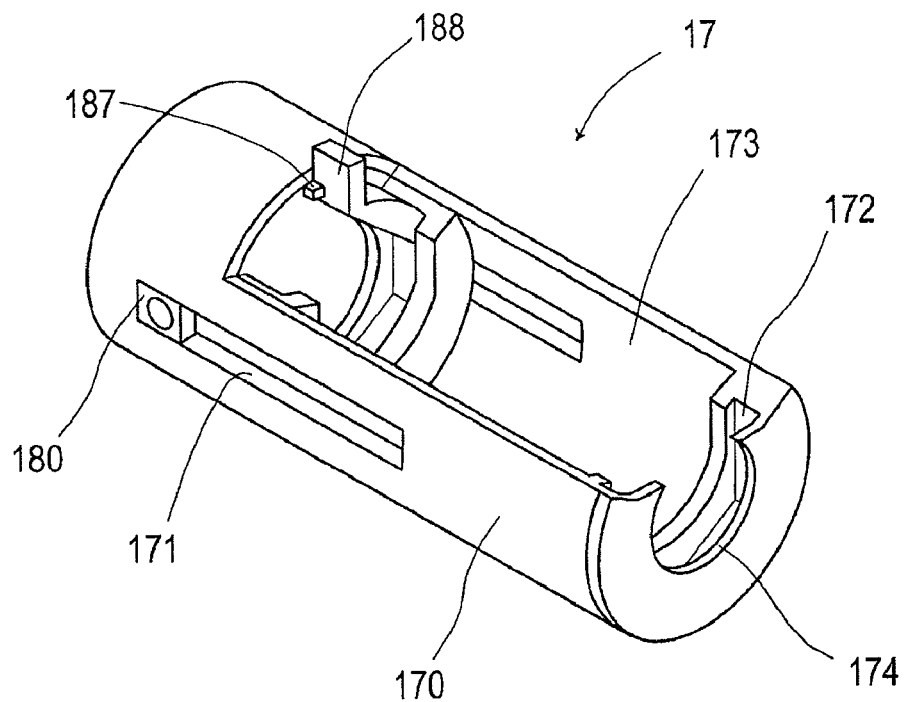
FIG. 22 is a second perspective view of a cap to which a joint is assembled in example 1.

As shown in FIGS. 21 and 22, the cap section 17 of this example is a part placed around the joint 18 in which the rotation member 182 is assembled. The cap section 17 is a member consisting of a substantially cylindrical part positioned on the medication pen 2 side and an incomplete cylindrical part provided with an opening part 173 for setting the injection needle cartridge 1 from the outside.

The cap section 17 has, on an outer peripheral surface 170 thereof, a slit groove 171 for advancing and retreating the convex part 180 of the joint 18 in the axial direction. Also, in the bottom portion of the cap section 17, that is, in the end portion on the front end side of the medication pen 2, a holding part 172 for restricting the rotation and axial displacement of the hexagonal bottom plate 120 of the second holder member 12 is formed. In the bottom surface of the cap section 17, a through hole 174 for allowing the injection needle of the injection needle cartridge 1 to penetrate through is formed.

Figure 23:
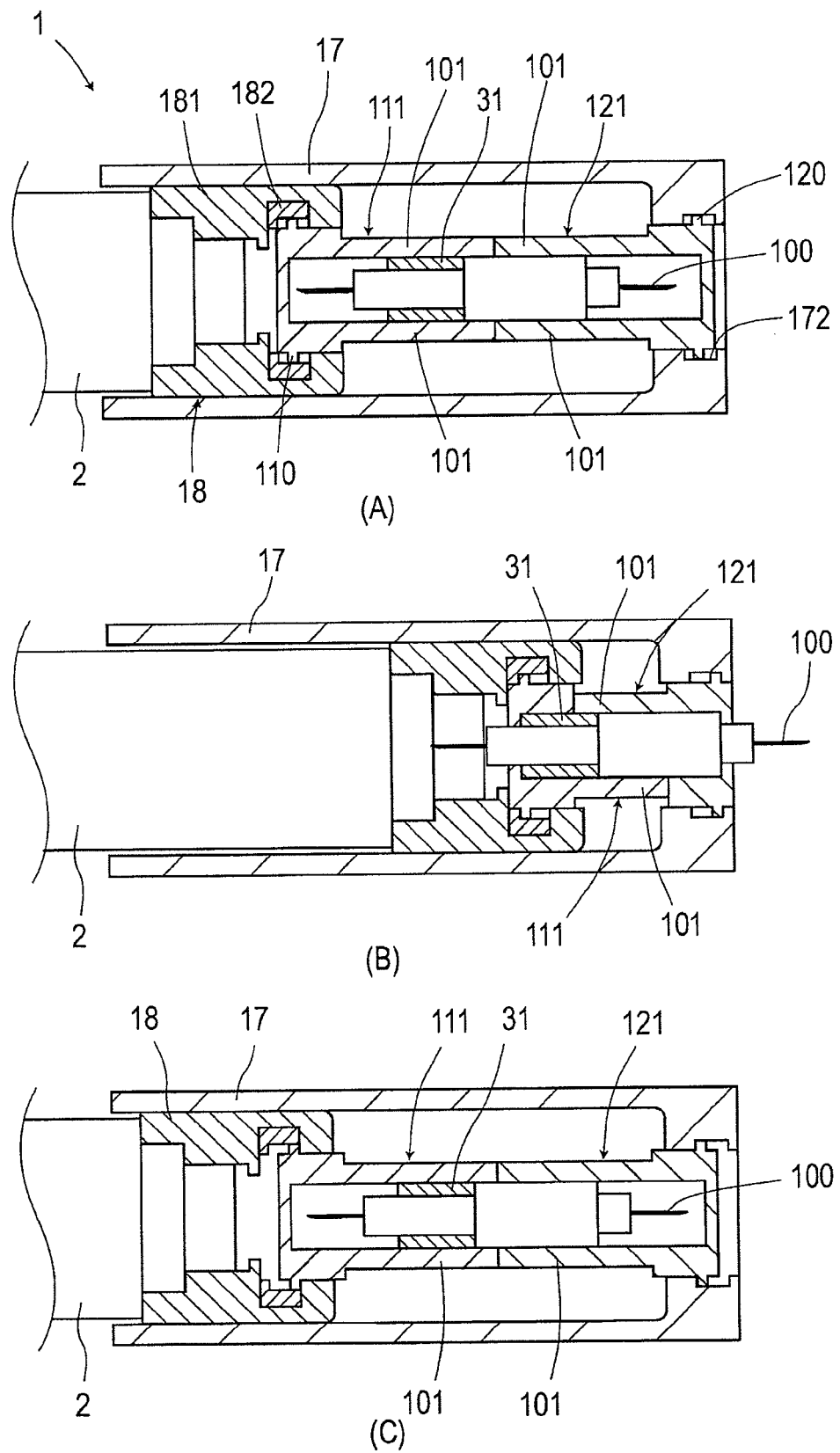
FIG. 23 is sectional views showing cross-sectional constructions of an injection needle cartridge in example 1.
Figure 24:
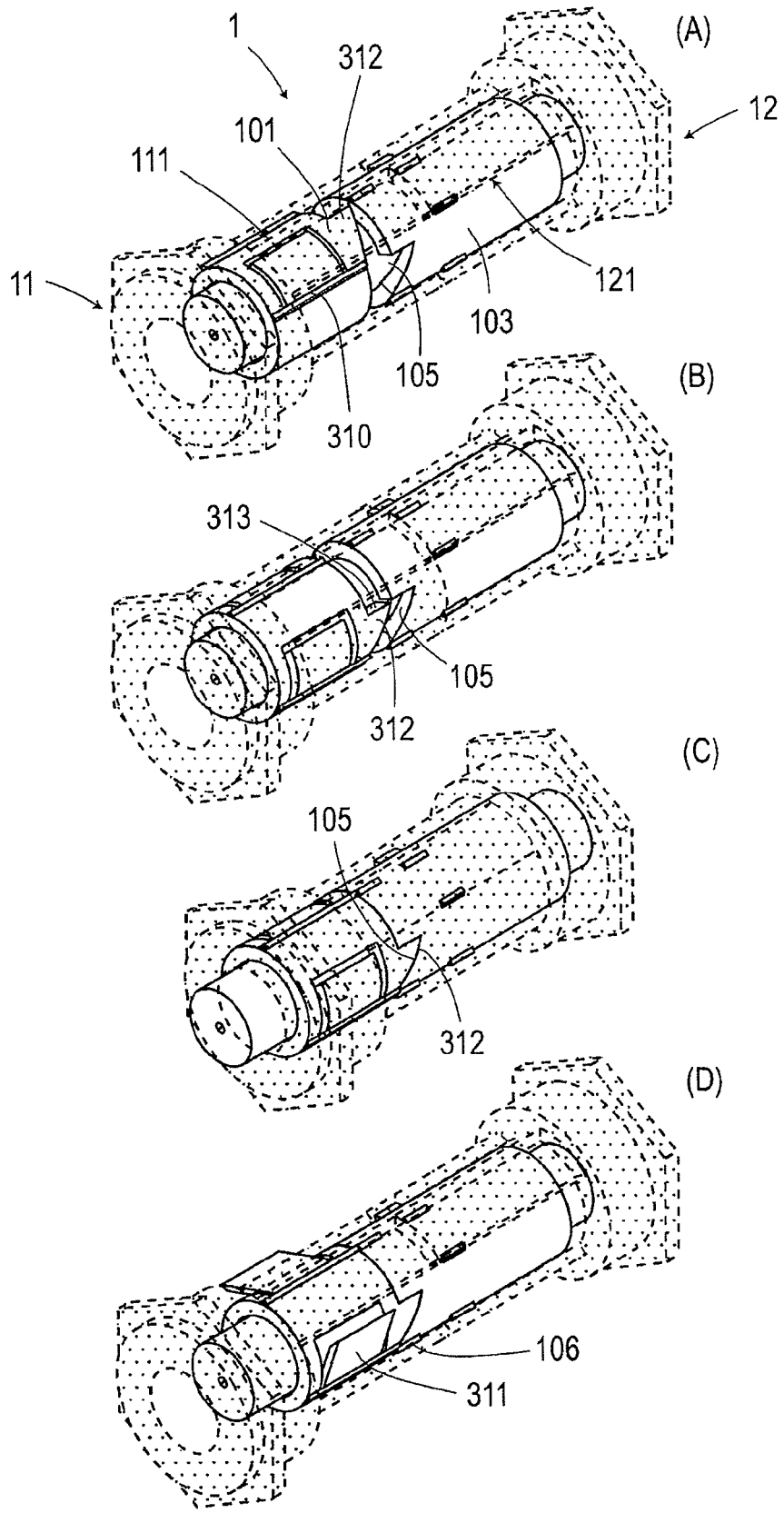
FIG. 24 is explanatory views for explaining the operation sequence of an injection needle cartridge in example 1.
Figure 25:
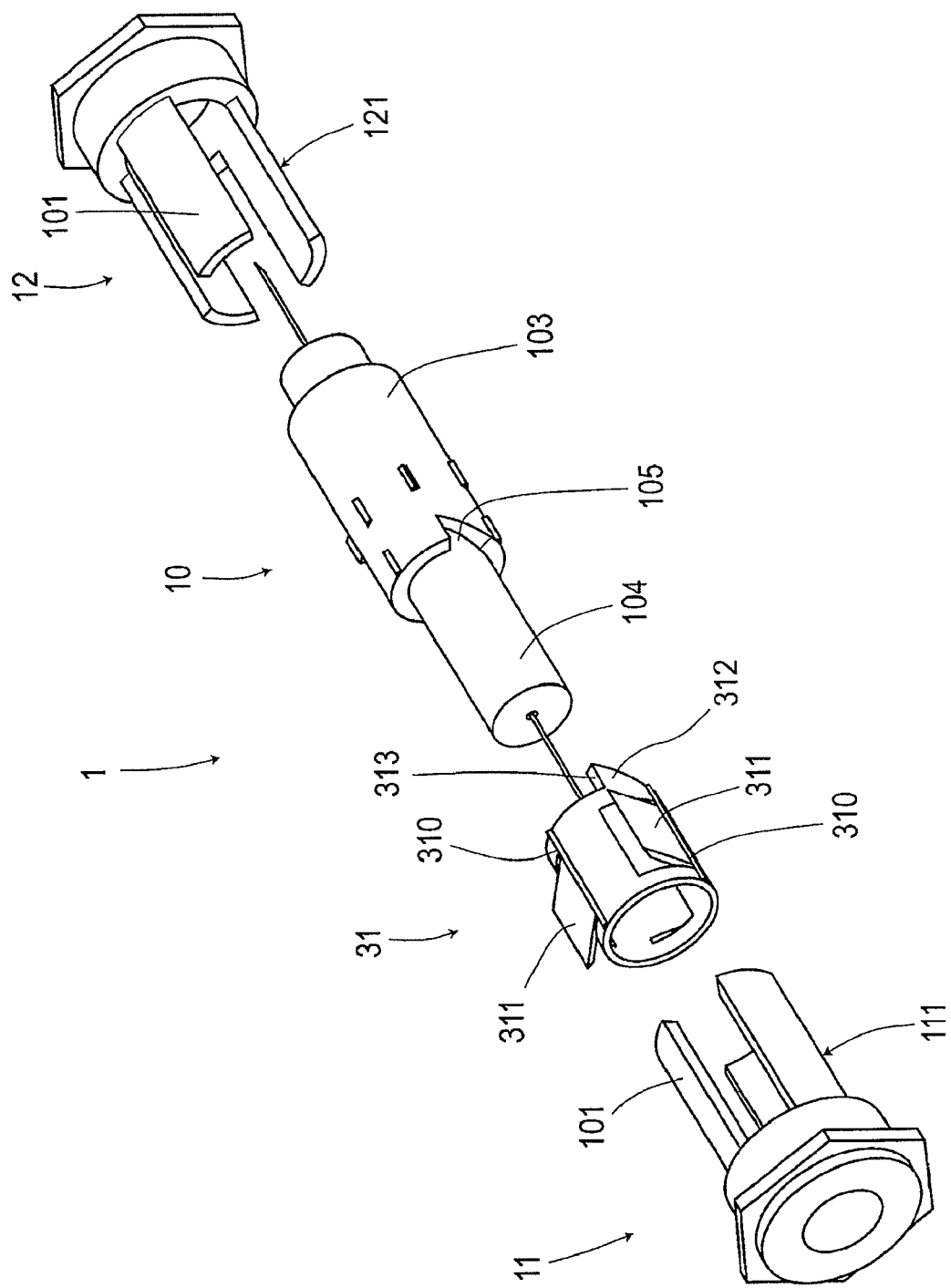
FIG. 25 is an exploded view showing a construction of an injection needle cartridge being used in example 1.

The state in which the unused injection needle cartridge 1 is set on the medication pen 2 of this example is the state shown in FIG. 23(A). The injection needle cartridge 1 in this state is in the state shown in FIGS. 18 and 24(A). The injection needle cartridge 1 in this state is in the state in which the slider sections 111 and 121 of the holder members 11 and 12 face to each other, and are in a not axially retractable state. FIG. 23 shows a sectional shape by setting a section such that two pillar-shaped parts 101 of each of the holder members 11 and 12 can be shown in the state in which the slider sections 111 and 121 face to each other (FIGS. 23(A) and 23(C)). Also, in FIG. 24, the holder members 11 and 12 are shown by dotted lines and a dot hatch.

When the rotation member 182 is turned from the rotation position shown in FIG. 21 to the rotation position shown in FIG. 22, the first holder member 11 can be turned with respect to the second holder member 12 whose rotation is restricted. At this time, as shown in FIGS. 18 and 24(A), by the engagement of the pillar-shaped parts 101 constituting the first slider section 111 with the detent 310, the inner ring 31 turns together. Thereby, the injection needle cartridge 1 is made in the state shown in FIG. 25, which is an exploded view, and FIG. 24(B). The injection needle cartridge 1 in this state is in the state in which the slider sections 111 and 121 of the holder members 11 and 12 are alternately displaced in a comb tooth form, and are in an axially retractable state. Further, in this state, as shown in FIG. 24(B), the injection needle cartridge 1 is in a state in which the circumferential position of the engagement convex part 312 of the inner ring 31 and the circumferential position of the engagement concave part 105 of the large-diameter part 103 substantially coincide with each other.

In this state, as shown in FIGS. 23(B) and 24(B), the pair of holder members 11 and 12 are axially retractable by means of the construction in which the slider sections 111 and 121 are engaged with each other alternately in a comb tooth form. When the injection needle cartridge 1 is retracted in the axial direction by inserting the medication pen 2 deeply into the cap section 17, the injection needle 100 is projected to both end sides, by which an injectable state can be formed. Also, when the injection needle cartridge 1 is retracted in the axial direction, as shown in FIG. 24(C), the inner ring 31 moves to the inside in the axial direction, and the engagement convex part 312 thereof fits in the engagement concave part 105 of the large-diameter part 103.

Thereafter, by pulling the medication pen 2 out of the cap section 17, the injection needle cartridge 1 is extended in the axial direction, and a lap portion in the axial direction of the first slider section 111 and the second slider section 121 is eliminated, by which a state in which the pair of holder members 11 and 12 can be turned relative to each other is formed. At this time, the state in which the engagement convex part 312 of the inner ring 31 and the engagement concave part 105 of the large-diameter part 103 engage with each other (refer to FIG. 24(C)) is still maintained. When the rotation member 182 is turned from the rotation position shown in FIG. 22 to the rotation position shown in FIG. 21 in this state, the first holder member 11 can be turned relative to the second holder member 12 whose rotation is restricted. At this time, the inner ring 31 engaging with the engagement concave part 105 of the large-diameter part 103 cannot turn together with the first holder member 11, and only the first holder member 11 turns. Thereby, a state in which the slider sections 111 and 121 face to each other, and the injection needle cartridge 1 is not axially retractable as shown in FIG. 24(D) can be formed.

Figure 26:
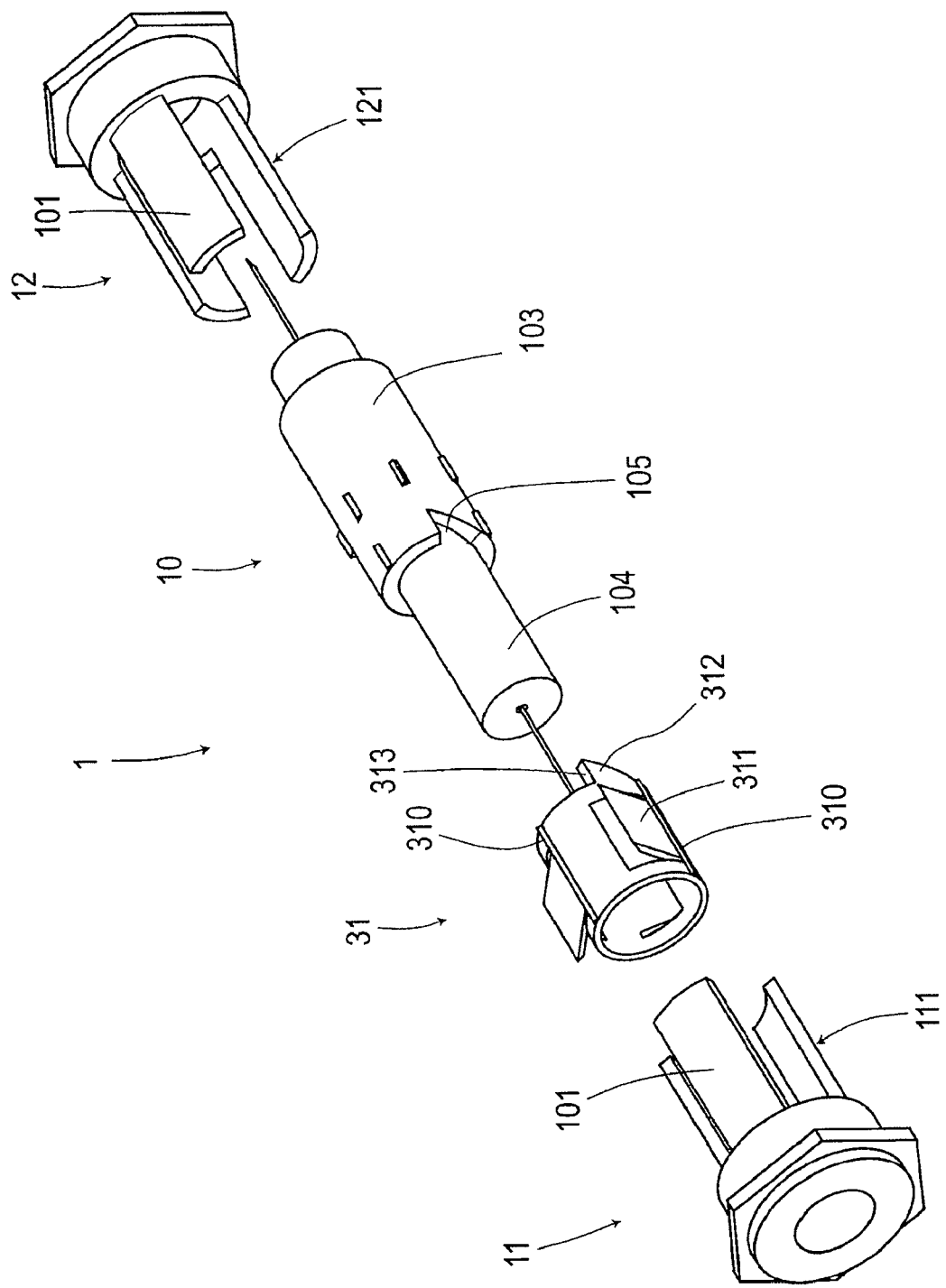
FIG. 26 is an exploded view showing a construction of an injection needle cartridge after being used in example 1.

At this time, as shown in FIG. 24(D) and FIG. 26, which is an exploded view, the engagement pieces 311 released from the pressing force due to the pillar-shaped parts 101 of the first slider section 111 are opened toward the outside. By the opened engagement pieces 311, the relative rotation of the first holder member 11 restoring to the state shown in FIG. 24(B) can be restricted with high reliability. On the other hand, the reverse relative rotation of the first holder member 11 is restricted with high reliability by the engagement of the convex part 106 of the retaining member 10 with the pillar-shaped parts 101 of the first slider section 111. Therefore, the used injection needle cartridge 1 can keep, with high reliability, the state in which the slider sections 111 and 121 face to each other and are not axially retractable.

As described above, according to the injection needle cartridge 1 and the medication pen 2 of this example, the used injection needle cartridge 1 can be disposed of with high safety. In particular, for the medication pen 2 of this example, the used injection needle cartridge 1 can keep the not axially retractable state with high reliability by the operation of the inner ring 31. Therefore, if this injection needle cartridge 1 is used, a possibility of the occurrence of secondary infection and the like caused, for example, by a needle stick accident can be prevented effectively.

A storage section for storing spare injection needle cartridges 1 may be provided in the cap section 17 or the like. In this case, the spare injection needle cartridges 1 are easily carried with the user.

Example 2

Example 2 is an example in which based on example 1, an engagement part engaging with the opposed slider section is provided in each of the slider sections. The details thereof are explained with reference to FIGS. 27 and 28.

The holder member 11 (12) of this example has an engagement part 112 (122), which engages with the pillar-shaped part 101 of the opposed slider section 121 (111), at the extreme end of the pillar-shaped part 101 constituting the slider section 111 (121).

Figure 27:
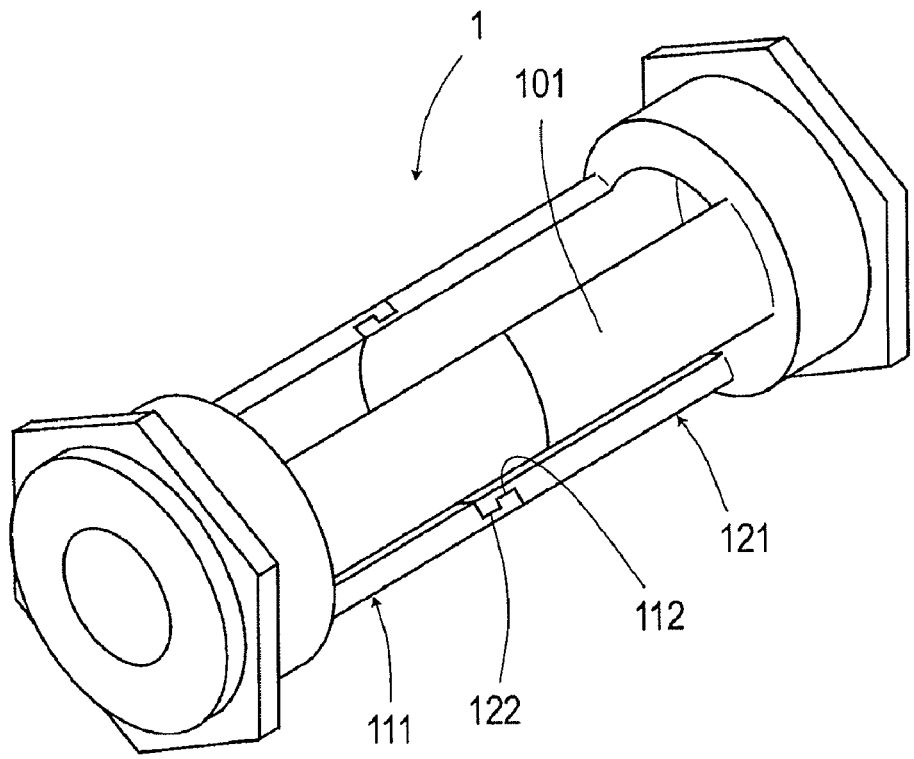
FIG. 27 is a perspective view showing an engaged state of a pair of slider sections in example 2, in which a retaining member is omitted.
Figure 28:
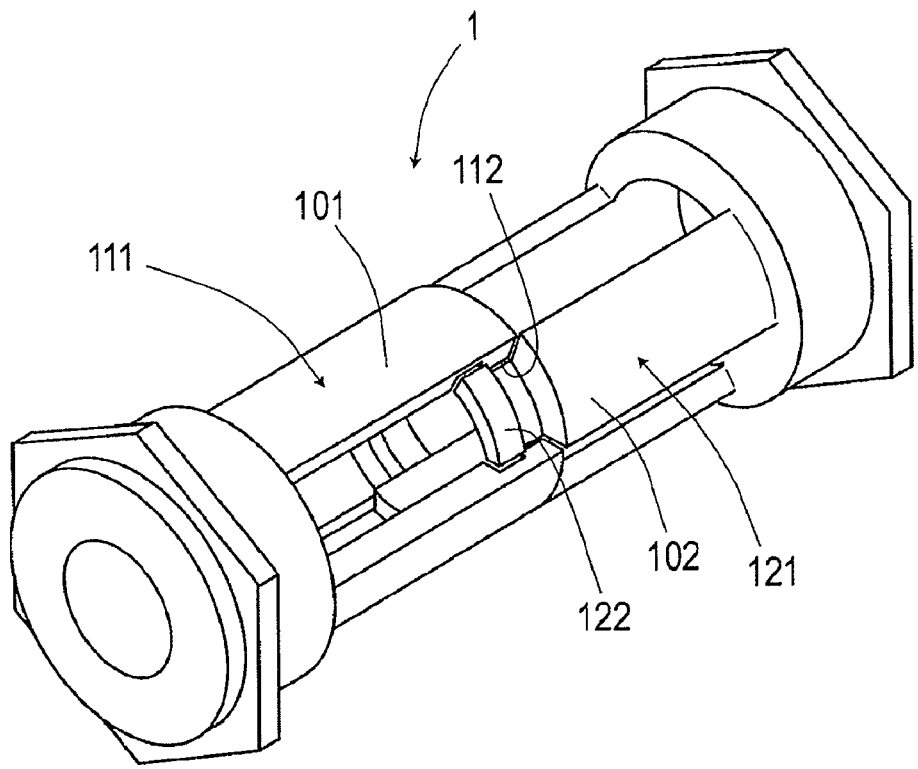
FIG. 28 is a perspective view showing a disengaged state of a pair of slider sections in example 2, in which a retaining member is omitted.

As shown in FIG. 27, in the state in which the engagement parts 112 and 122 are engaged with each other, and the slider sections 111 and 121 face to each other, a state in which the injection needle cartridge 1 is in a not axially retractable state, and the injection needle cartridge 1 cannot be extended can be formed. On the other hand, when the slider sections 111 and 121 are turned relative to each other as shown in FIG. 28, the engaged state of the engagement parts 112 and 122 can be released, and an axially retractable state can be formed. In FIGS. 27 and 28, the retaining member is omitted.

Other configurations and operational advantages are the same as those of example 1.

Example 3

Figure 29:
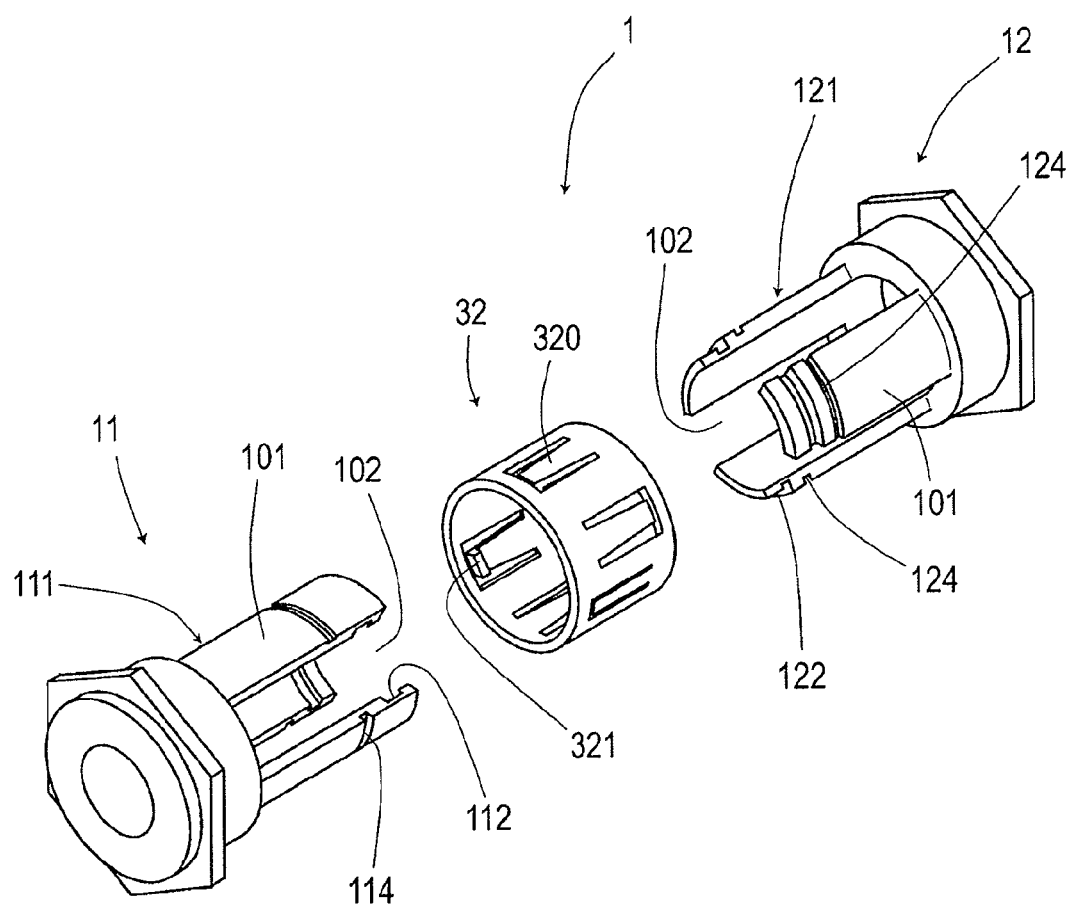
FIG. 29 is an exploded assembly view showing an assembling construction of an injection needle cartridge in example 3, in which a retaining member is omitted.

Example 3 is an example in which based on example 2, an outer ring 32 serving as an extension restricting mechanism for restricting the maximum axial separation distance of the pair of holder members 11 and 12 is added. The details thereof are explained with reference to FIG. 29. In FIG. 29, the retaining member is omitted.

As shown in FIG. 29, the outer ring 32 is a substantially cylindrical member that is placed around the slider sections 111 and 121 of the holder members 11 and 12.

The outer ring 32 has lock pieces 320 formed by cutting the outer peripheral surface into a U shape and arranged at intervals of 60 degrees. Each of the lock pieces 320 is extendingly provided along the axial direction, and the orientation in the axial direction of the root thereof is changed alternately. On the extreme end side of the lock piece 320, a hook-like part 321 projecting toward the inner periphery side is formed.

On the other hand, the pillar-shaped parts 101 of the slider sections 111 and 121 of this example have concave groove parts 114 and 124, with which the hook-like part 321 engages, respectively, in the outer peripheral surface close to the extreme end thereof. The groove part 114, 124 is extendingly provided along the circumferential direction, and is formed over the whole region in the width direction of the pillar-shaped part 101. The groove part 114, 124 allows the circumferential displacement of the engaging hook-like part 321. Therefore, in the injection needle cartridge 1 of this example, the holder members 11 and 12 can be turned relative to each other even in the state in which the hook-like parts 321 are engaged with the groove parts 114 and 124.

In the injection needle cartridge 1 after the outer ring 32 is placed, when an attempt is made to extend the pair of holder members 11 and 12 in the state in which the slider sections 111 and 121 are engaged with each other in a comb tooth form, the maximum separation distance of the pair of holder members 11 and 12 can be restricted with high reliability by the engagement of the hook-like parts 321 of the lock pieces 320 with the groove parts 114 and 124. Further, in the injection needle cartridge 1 in which the outer ring 32 is placed around the slider sections 111 and 121, mischief such that the pillar-shaped part 101 of the slider section 111, 121 is bent to the outer periphery side can be prevented.

Other configurations and operational advantages are the same as those of example 2.

Example 4

Example 4 is an example in which based on the injection needle cartridge of example 1, a surrounding ring 33 is used in place of the inner ring and the outer ring. The details thereof are explained with reference to FIGS. 30 to 33.

Figure 30:
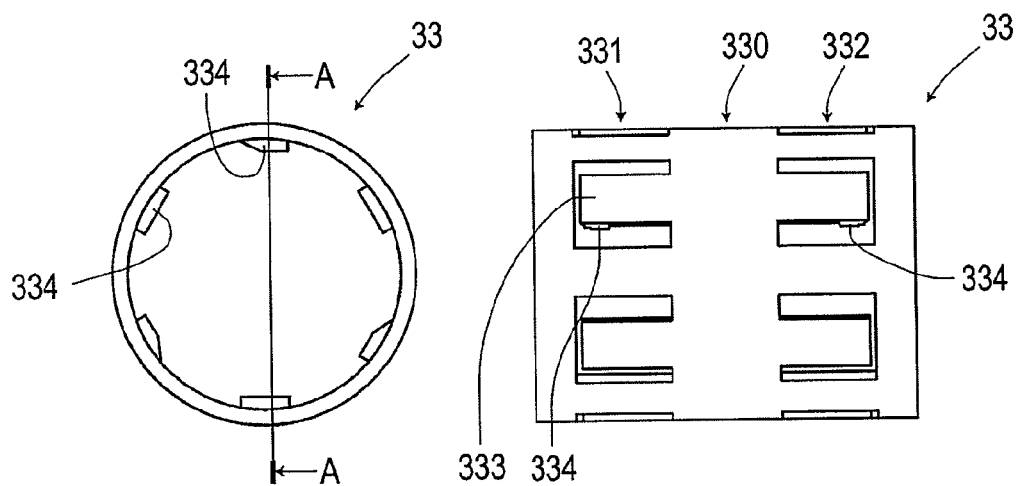
FIG. 30 is views of a surrounding ring in example 4.
Figure 31:
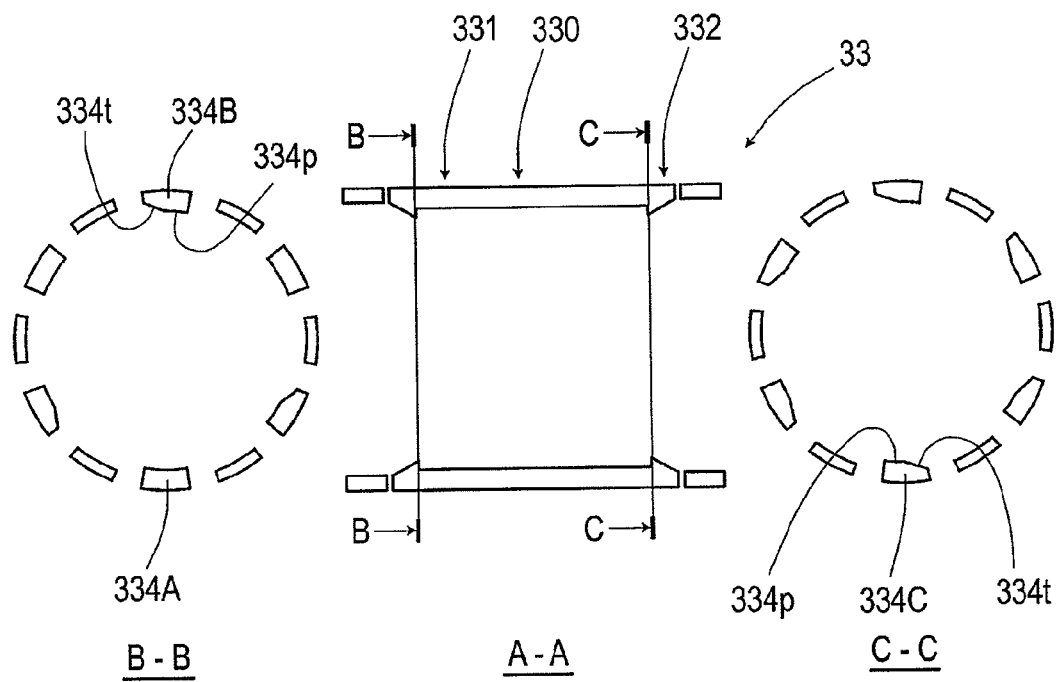
FIG. 31 is views showing a cross-sectional construction of a surrounding ring in example 4.

As shown in FIGS. 30 and 31, the surrounding ring 33 is a substantially cylindrical ring placed around the slider sections 111 and 121 of the holder members 11 and 12. In the surrounding ring 33, a first formation part 331 is positioned on the first holder member 11 side and a second formation part 332 is positioned on the second holder member 12 side with a middle part 330 in the axial direction being the center. Each of the first formation part 331 and the second formation part 332 is formed with six lock pieces 333 arranged at substantially equal intervals in the circumferential direction. Each of the lock pieces 333 is a part formed by cutting the outer peripheral wall of the first formation part 331 or the second formation part 332 so that the middle part 330 side is a root. The circumferential formation positions of the lock pieces 333 of the first formation part 331 and those of the second formation part 332 substantially coincide with each other. Also, in the sectional views of the first formation part 331 and the second formation part 332, the sections of the lock piece 333 and the outer peripheral wall sections of the first formation part 331 or the second formation part 332 appear alternatively.

Each of all the lock pieces 333 is formed with a hook-like part 334 projecting toward the inner periphery side on the extreme end side thereof. The hook-like part 334 is a part in which in a cross section including the axis, the projection height increases gradually toward the middle part 330, and which has a substantially wedge-shaped cross-sectional shape forming the inner peripheral end face perpendicular to the axis direction.

Between the first formation part 331 and the second formation part 332, the shape and configuration of the hook-like part 334 differs. First, the hook-like part 334 that the first formation part 331 has is explained. As the hook-like part 334 of the first formation part 331, two kinds of hook-like parts are present. A first hook-like part 334A is a hook-like part in which the projection height toward the inner periphery side is substantially constant in the circumferential direction as shown in the B-B sectional view in FIG. 31. A second hook-like part 334B is a hook-like part including a part 334*p* in which the projection height toward the inner periphery side is substantially constant in the circumferential direction and an inclined part 334*t* in which the projection height gradually decreases in the circumferential direction from the part 334*p* as shown in the B-B sectional view in FIG. 31. In the second hook-like part 334B in the first formation part 331, the inclined part 334*t* is arranged on the left rotation side in the B-B sectional view in FIG. 31.

All of hook-like parts 334C in the second formation part 332 have the same specifications. As shown in the C-C sectional view in FIG. 31, the hook-like part 334C is a hook-like part including the part 334p in which the projection height toward the inner periphery side is substantially constant and the inclined part 334t in which the projection height gradually decreases in the circumferential direction from the part 334p. In the second hook-like part 334C in the second formation part 332, the inclined part 334t is arranged on the left rotation side like the second hook-like part 334B of the first formation part 331.

Figure 32:
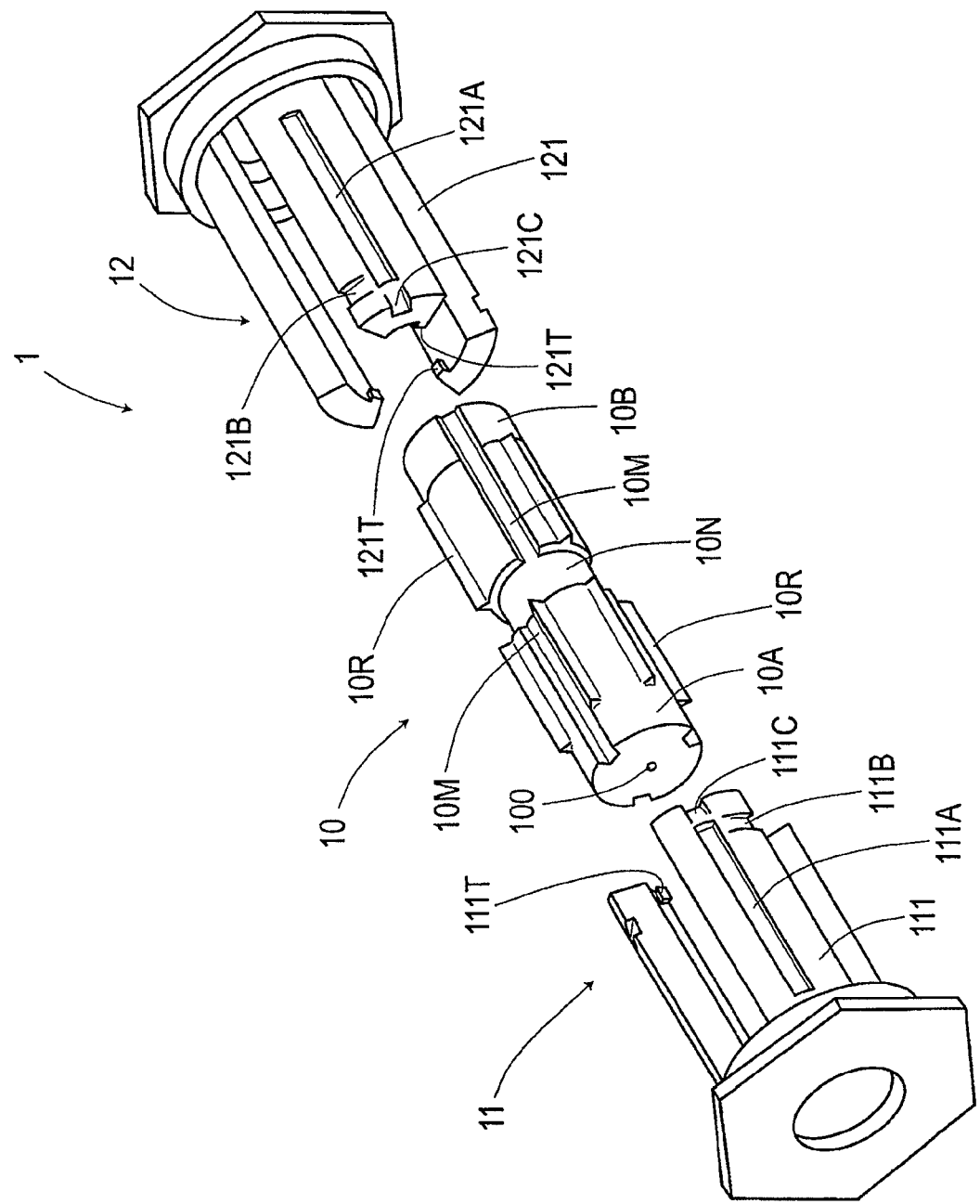
FIG. 32 is an exploded assembly view showing an assembling construction of an injection needle cartridge in example 4, in which a surrounding ring is omitted.

As shown in FIG. 32, the holder members 11 and 12 have almost the same specifications. The holder member of this example differs from that of example 1 in that three kinds of grooves 111A to 111C, 121A to 121C are provided in the outer peripheral surface of the slider section 111, 121, and that a convex part 111T, 121T is provided on the inner peripheral surface in the extreme end portion of the slider section 111, 121. In FIG. 32, only the position of the root of the needle 100 is shown, and the illustration of the projecting portion thereof is omitted.

First, the specifications of the convex part 111T, 121T is explained. One convex part 121T is formed on each of the inner peripheral surfaces of the slider section 111, 121. The convex part 111T, 121T is formed so as to project toward the axis. The inside diameter formed by the projection extreme end faces of the three convex parts 111T, 121T of the holder member 11, 12 is approximately equal to the outside diameter of a small-diameter part 10N of the retaining member 10, described later.

Also, a first groove among the three-kinds of grooves provided in the outer peripheral surface of the slider section 111, 121 is an advance/retreat groove 111A, 121A formed along the axial direction at a substantially central position in the circumferential direction as shown in FIG. 32. This advance/retreat groove 111A, 121A starts at a position near the root of the slider section 111, 121 and terminates at a position near the extreme end thereof. The advance/retreat groove 111A, 121A is a groove for allowing the hook-like part 334A to advance and retreat when the pair of holder members 11 and 12 extend or retract in the axial direction A second groove among the three kinds of grooves is a tapered groove 111B, 121B formed so as to become deeper gradually along the circumferential direction and to open to the circumferential end face of the slider section 111, 121 as shown in FIG. 32. This tapered groove 111B, 121B is formed so as to become deeper gradually in the left rotation direction with respect to the viewing direction in which the bottom plate 110, 120 is viewed from the extreme end side of the slider section 111, 121. The tapered groove 111B, 121B is formed on the left rotation side with respect to the viewing direction with some clearance being provided in the circumferential direction with respect to the advance/retreat groove 111A. The tapered groove 111B, 121B forms a slant surface for allowing the hook-like part 334 to ride when the holder member 11 or the holder member 12 turns relative to the surrounding ring 33.

A third groove among the three kinds of grooves is a tapered groove 111C, 121C formed so as to become deeper gradually toward the extreme end side in the axial direction and to open to the extreme end face of the slider section 111, 121 as shown in FIG. 32. This tapered groove 111C, 121C is formed so that the circumferential position thereof substantially coincides with that of the advance/retreat groove 111A, 121A, and that some clearance is provided in the axial direction with respect to the advance/retreat groove 111A, 121A. The tapered groove 111C, 121C forms a slant surface for allowing the hook-like part 334 to ride when the holder member 11, 12 is assembled to the surrounding ring 33.

As shown in FIG. 32, the retaining member 10 of this example has the small-diameter part 10N substantially in the middle in the axial direction, and has a first barrel 10A and a second barrel 10B having the almost the same diameter on both sides in the axial direction via this small-diameter part 10N. The first barrel 10A is positioned on the first holder member 11 side, and the second barrel 10B is positioned on the second holder member 12 side. On the outer peripheral surface of the first barrel 10A, ridge parts 10R projecting to the outer periphery side are formed at six places at substantially equal intervals in the circumferential direction. The ridge parts 10R are formed along the axial direction. Further, in the outer peripheral surface of the first barrel 10A, groove-shaped advance/retreat grooves 10M are formed along the axial direction at three places at substantially equal intervals in the circumferential direction. This advance/retreat groove 10M is a groove for allowing the convex part 121T formed on the inner peripheral surface of the second slider section 121 to advance and retreat.

On the outer peripheral surface of the first barrel 10A, six surface parts held between the adjacent ridge parts 10R in the circumferential direction are formed. In every other surface part of the six surface parts, the advance/retreat groove 10M is formed. Each of the three surface parts in which the advance/retreat groove 10M is not formed is a surface part with which the first slider section 111 makes contact externally. The six ridge parts 10R in the circumferential direction are formed so as to restrict the relative rotation of the first holder member 11 with respect to the first barrel 10A. The advance/retreat groove 10M is a groove for allowing the convex part 121T formed on the inner peripheral surface of the second slider section 121 to advance and retreat when the second holder member 12 advances and retreats in the axial direction with respect to the retaining member 10.

As shown in FIG. 32, on the outer peripheral surface of the second barrel 10B, ridge parts 10R projecting to the outer periphery side are formed at three places at substantially equal intervals in the circumferential direction. The ridge parts 10R are formed along the axial direction. Further, in the outer peripheral surface of the second barrel 10B, groove-shaped advance/retreat grooves 10M are formed along the axial direction at three places at substantially equal intervals in the circumferential direction. The advance/retreat grooves 10M of the second barrel 10B are formed shifting through about 60 degrees from the advance/retreat grooves 10M of the first barrel 10A. The advance/retreat groove 10M is a groove for allowing the convex part 111T formed on the inner peripheral surface of the first slider section 111 to advance and retreat when the first holder member 11 advances and retreats in the axial direction with respect to the retaining member 10.

On the outer peripheral surface of the second barrel 10B, three surface parts held between the adjacent ridge parts 10R in the circumferential direction are formed. These three surface parts are formed at intervals of about 120 degrees in the circumferential direction. On the other hand, the circumferential width of the second slider section 121 is about 60 degrees in the circumferential direction. That is to say, the second barrel 10B is formed so as to allow the relative rotation of the second holder member 12 in the range of about 60 degrees.

Figure 33:
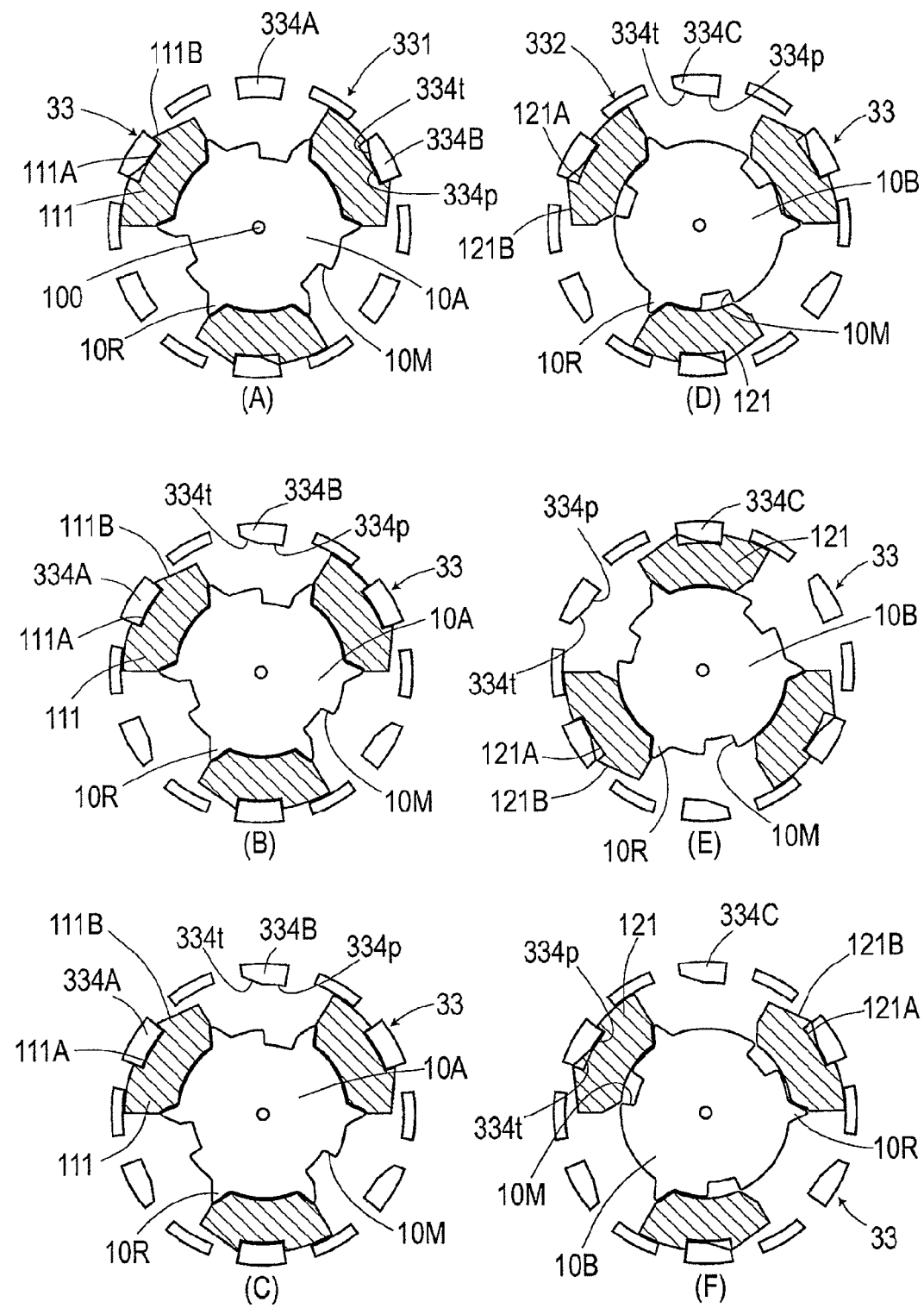
FIG. 33 is explanatory views showing the operation of an injection needle cartridge in example 4.

Next, the operation of the injection needle cartridge 1 of this example in which the retaining member 10, the holder members 11 and 12, and the surrounding ring 33 configured as described above are combined, and especially the operation of the rotation restricting mechanism that this injection needle cartridge 1 has are explained with reference to FIG. 33. In this figure, FIGS. 33(A) to 33(C) in the left column are sectional views showing cross sections including the tapered grooves 111B of the first holder member 11. In FIG. 33, FIGS. 33(d) to 33(F) in the right column are sectional views showing cross sections including the tapered grooves 121B of the second holder member 12. All of these sectional views show cross-sectional constructions at the time when the second holder member 12 side is viewed from the first holder member 11 side.

First, FIGS. 33(A) and 33(D) in the uppermost row in FIG. 33 are sectional views showing cross-sectional constructions in an unused state (assembled state). Of these two figures, FIG. 33(A) on the left-hand side shows the first formation part 331 of the surrounding ring 33, the slider section 111 of the first holder member 11, and the first barrel 10A of the retaining member 10 arranged from the outer periphery side. FIG. 33(D) on the right-hand side shows the second formation part 332 of the surrounding ring 33, the slider section 121 of the second holder member 12, and the second barrel 10B of the retaining member 10 arranged from the outer periphery side. In this state, the circumferential position of the slider section 111 of the first holder member 11 substantially coincides with that of the slider section 121 of the second holder member 12. That is to say, in this state, the extreme end face of the slider section 111 and that of the slider section 121 face to each other and the slider sections 111 and 121 are in a not axially retractable state.

As shown in FIG. 33(A), the slider section 111 is externally in contact with the outer peripheral surface in which the advance/retreat groove M is not formed of the six surface parts defined in the circumferential direction by the ridge parts 10R on the outer peripheral surface of the first barrel 10A. In the advance/retreat groove 111A in the outer peripheral surface of the slider section 111, the second hook-like part 334B of the surrounding ring 33 (the first formation part 331) is accommodated. As described above, in the second hook-like part 343B, the inclined part 334t is arranged on the left rotation side.

Also, as shown in FIG. 33(D), the second slider section 121 is externally in contact with the outer peripheral surface of the three surface parts defined by the ridge parts 10R on the outer peripheral surface of the second barrel 10B. The injection needle cartridge 1 is in the state in which the second holder member 12 is fully turned to the right rotation side with respect to the outer peripheral surface of 120 degrees in the circumferential direction. In the advance/retreat groove 10M in the outer peripheral surface of the slider section 121, the hook-like part 334C of the surrounding ring 33 (the second formation part 332) is accommodated. As described above, in the hook-like part 334C, the inclined part 334t is formed on the left rotation side.

In using the injection needle cartridge 1, the second holder member 12 is turned through about 60 degrees in the left rotation direction in FIG. 33 with respect to the first holder member 11 and the retaining member 10. When the second holder member 12 is turned to the left, the surrounding ring 33 also tends to be turned by the engagement construction of the hook-like part 334C with the advance/retreat groove 121A. As shown in FIG. 33(A), in the second hook-like part 334B engaging with the advance/retreat groove 111A of the first slider section 111, the inclined part 334t is formed on the left rotation side. Also, in the first slider section 111, the circumferential tapered grooves 111B are formed on the right rotation side.

Therefore, the surrounding ring 33 can be turned in association with the left rotation of the second holder member 12. When the surrounding ring 33 turns to the left, as shown in FIG. 33(A), the second hook-like part 334B can escape from the advance/retreat groove 111A by using the inclined part 334t, and the first hook-like part 334A goes into the advance/retreat groove 111A by using the slant surface shaped bottom surface of the tapered groove 111B, by which the second holder member 12 is turned to the left relative to the surrounding ring 33.

When the second holder member 12 is turned to the left together with the surrounding ring 33 as described above, the state shown in FIGS. 33(B) and 33(E) is realized. In this state, the circumferential position of the slider section 111 of the first holder member 11 and that of the slider section 121 of the second holder member 12 differ from each other. That is to say, this state is a state in which the slider section 111 and the slider section 121 are alternately displaced and are axially retractable.

Also, as shown in FIG. 33(B), the first hook-like part 334A of the surrounding ring 33 (the first formation part 331) is accommodated in the advance/retreat groove 111A in the outer peripheral surface of the slider section 111 unlike the case shown in FIG. 33(A). Also, as shown in FIG. 33(E), the second holder member 12 is in a state of being turned fully to the left rotation side with respect to the outer peripheral surface of 120 degrees in the circumferential direction defined by the ridge parts 10R. At the stage from FIG. 33(D) to FIG. 33(E), a change of the hook-like part 334C accommodated in the advance/retreat groove 121A in the outer peripheral surface of the second slider section 121 does not occur. The important point is that in the hook-like part 334C accommodated in the advance/retreat groove 121A of the slider section 121, the inclined part 334t is formed on the left rotation side.

After the use, the second holder member 12 is turned again through 60 degrees to the right in FIG. 33. At this time, as described above, the hook-like part accommodated in the advance/retreat groove 111A of the first slider section 111 is the first hook-like part 334A not having the inclined part 334t (FIG. 33(B)). This first hook-like part 334A is a hook-like part that cannot escape from the advance/retreat groove 111A according to the relative rotational force with respect to the first holder member 11. Therefore, in the state shown in FIG. 33(B), the injection needle cartridge 1 is in the state in which the relative rotation of the first holder member 11 and the surrounding ring 33 is restricted.

On the other hand, as shown in FIG. 33(E), the hook-like part 334C accommodated in the advance/retreat groove 121A of the second slider section 121 is formed with the inclined part 334t on the left rotation side. Therefore, when the second holder member 12 is turned to the right, the hook-like part 334C can escape from the advance/retreat groove 121A by using the inclined part 334t. When the second holder member 12 is turned to the right relative to the surrounding ring 33, the second slider section 121 comes close to the new hook-like part 334C. Since this hook-like part 334C also has the inclined part 334t on the left rotation side, the hook-like part 334C can go into the advance/retreat groove 121A of the slider section 121 by using this inclined part 334t. Therefore, when the second holder member 12 is turned to the right in the state shown in FIG. 33(E), the surrounding ring 33 does not turn together with the second holder member 12, and only the second holder member 12 can be turned.

When the second holder member 12 is turned to the right in FIG. 33 based on the state shown in FIGS. 33(B) and 33(E), the state shown in FIGS. 33(C) and 33(F) can be obtained. In this state, the circumferential position of the slider section 111 of the first holder member 11 and that of the slider section 121 of the second holder member 12 substantially coincide with each other. That is to say, in this state, the injection needle cartridge 1 is in the state in which the extreme end face of the slider section 111 and that of the slider section 121 face to each other, and the slider section 111 and the slider section 121 are not axially retractable.

As shown in FIG. 33(C), in the advance/retreat groove 111A of the first slider section 111, the first hook-like part 334A not having the inclined part 334t is accommodated. Therefore, in this state, the surrounding ring 33 cannot turn relative to the first holder member 11. Further, since six ridge parts 10R are formed at the outer periphery of the first barrel 10A, the first holder member 11 also cannot turn relative to the retaining member 10.

Furthermore, as shown in FIG. 33(F), in the advance/retreat groove 121A of the second slider section 121, the hook-like part 334C having the inclined part 334t on the left rotation side is accommodated. Based on the relationship only between the advance/retreat groove 121A and the hook-like part 334C, the second holder member 12 seems to be capable of being turned to the right. However, in this state, the injection needle cartridge 1 is in the state in which the second slider section 121 is in contact with the ridge part 10R on the right rotation side. Therefore, based on the relationship with the retaining member 10, the right rotation of the second holder member 12 is restricted.

As shown in FIGS. 33(C) and 33(F), when the second holder member 12 is turned to the right after the use, a state in which the first holder member 11 and the second holder member 12 cannot be turned relative to each other by the action of the rotation restricting mechanism formed including the surrounding ring 33 is formed. Further, in this state, the circumferential position of the advance/retreat groove 10M of the first barrel 10A and that of the convex part 111T of the first holder member 11 are different from each other. Therefore, the convex part 111T engages with the end face (advance/retreat restricting part) between the small-diameter part 10N and the first barrel 10A, by which the axial withdrawal of the first holder member 11 from the retaining member 10 is restricted.

Also, in the state shown in FIGS. 33(C) and 33(F), the circumferential position of the advance/retreat groove 10M of the second barrel 10B and that of the convex part 121T of the second holder member 12 are different from each other. Therefore, the convex part 121T engages with the end face (advance/retreat restricting part) between the small-diameter part 10N and the second barrel 10B, by which the axial withdrawal of the second holder member 12 from the retaining member 10 is restricted.

Other configurations and operational advantages are the same as those of example 1.

The invention claimed is:

1. An injection needle cartridge comprising:
a substantially columnar retaining member for retaining an injection needle axially penetrating therethrough so that the injection needle projects from both end surfaces thereof;
a first holder member having a first bottom plate facing to one end surface of the retaining member and a first slider section erected from the first bottom plate so as to be in contact with the outer peripheral side surface of the retaining member to hold the retaining member;
a second holder member having a second bottom plate facing to the other end surface of the retaining member and a second slider section erected from the second bottom plate so as to be in contact with the outer peripheral side surface of the retaining member to hold the retaining member, wherein the second holder member is configured to contain the retaining member in a containing space formed by the first bottom plate and the second bottom plate oriented to face to each other, and to be rotatable relative to the first holder member about the axis of the retaining member; and
a substantially cylindrical inner ring constituting a rotation restricting mechanism for restricting the relative rotation of the paired holder members about the axis of the retaining member in a state of being placed around the retaining member and positioned on the inner periphery side of the first slider section or the second slider section,
wherein the containing space is axially retractable in the state in which the slider sections are alternately displaced along the outer periphery of the retaining member to allow the injection needle of the retaining member to penetrate through and to project from the bottom surface plates to be capable of an injection, and
wherein the containing space is axially extendable to place the injection needle in the containing space after the injection, in which the cylindrical inner ring is configured to,
(i) allow the first and second holder members to rotate relative to each other to a position where the extreme end faces of the slider sections of the first and second holder members face to each other, and then
(ii) restrict the relative rotation of the first and second holder members in said position.

2. The injection needle cartridge according to claim 1, wherein
the injection needle cartridge is configured to be in the not axially retractable state when being in an unused state, be made in the axially retractable state by turning the paired holder members relative to each other when being in use, and be made capable of reestablishing the not axially retractable state by turning the paired holder members relative to each other again after being used; and
the rotation restricting mechanism is configured to allow the relative rotation of the paired holder members before the injection needle cartridge shifts to the axially retractable state, and restrict the relative rotation of the paired holder members after the injection needle cartridge shifts from the axially retractable state to the not axially retractable state.

3. The injection needle cartridge according to claim 1, wherein
the injection needle cartridge comprises a substantially cylindrical outer ring placed around the first and second slider sections; and
the outer ring has an extension restricting mechanism configured so that the maximum axial separation distance of the paired holder members can be restricted in the injection needle cartridge in the axially retractable state.

4. The injection needle cartridge according to claim 1, wherein
each of the slider sections has an engagement part which engages with the other of the slider sections in the state in which the extreme end faces of the slider sections face to each other; and
the injection needle cartridge is configured so that by engaging the slider sections with each other via the engagement parts, the relative advance and retreat in the axial direction of the paired holder members can be restricted.

5. The injection needle cartridge according to claim 1, wherein the injection needle cartridge has an airtight member for maintaining the sterilized state of the retaining member, and wherein the injection needle cartridge is configured so that the injection needle of the retaining member penetrates through and projects from the airtight member.

6. The injection needle cartridge according to claim 1, wherein in locations in which the retaining member and the slider sections are in contact with each other, a groove-shaped advance/retreat groove provided along the axial direction and a convex part which advances and retreats in a state of being accommodated in the advance/retreat groove are provided, and the advance/retreat groove is formed so as to prevent the convex part from coming off in the axial direction.

7. The injection needle cartridge according to claim 1, wherein
the injection needle cartridge comprises an applicator including a substantially cylindrical first member provided with an engagement part engaging with an injector on which the injection needle cartridge is to be mounted and a second member which is provided with a hollow part for allowing the first member to be inserted and advances and retreats in the axial direction with respect to the first member, the applicator being formed so as to be capable of accommodating the paired holder members and the retaining member integrally; and
the applicator is configured so that the paired holder members can be turned relative to each other by turning the second member relative to the first member, and the containing space can be retracted axially by the advance and retreat of the second member with respect to the first member.

8. An injection needle cartridge comprising:
a substantially columnar retaining member for retaining an injection needle axially penetrating therethrough so that the injection needle projects from both end surfaces thereof;
a first holder member having a first bottom plate facing to one end surface of the retaining member and a first slider section erected from the first bottom plate so as to be in contact with the outer peripheral side surface of the retaining member to hold the retaining member;
a second holder member having a second bottom plate facing to the other end surface of the retaining member and a second slider section erected from the second bottom plate so as to be in contact with the outer peripheral side surface of the retaining member to hold the retaining member, wherein the second holder member is configured to contain the retaining member in a containing space formed by the first bottom plate and the second bottom plate oriented to face to each other, and to be rotatable relative to the first holder member about the axis of the retaining member; and
a substantially cylindrical surrounding ring constituting a rotation restricting mechanism for restricting the relative rotation of the paired holder members in a state of being placed around the first and second slider sections,
wherein the containing space is axially retractable in the state in which the slider sections are alternately displaced along the outer periphery of the retaining member to allow the injection needle of the retaining member to penetrate through and to project from the bottom surface plates to be capable of an injection, and
wherein the containing space is axially extendable to place the injection needle in the containing space after the injection, in which the cylindrical surrounding ring is configured to,
(i) allow the first and second holder members to rotate relative to each other to a position where the extreme end faces of the slider sections of the first and second holder members face to each other, and then
(ii) restrict the relative rotation of the first and second holder members in said position.

9. The injection needle cartridge according to claim 8, wherein
the injection needle cartridge is configured to be in the not axially retractable state when being in an unused state, be made in the axially retractable state by turning the paired holder members relative to each other when being in use, and be made capable of reestablishing the not axially retractable state by turning the paired holder members relative to each other again after being used; and
the rotation restricting mechanism is configured to allow the relative rotation of the paired holder members before the injection needle cartridge shifts to the axially retractable state, and restrict the relative rotation of the paired holder members after the injection needle cartridge shifts from the axially retractable state to the not axially retractable state.

10. The injection needle cartridge according to claim 8, wherein the injection needle cartridge has an airtight member for maintaining the sterilized state of the retaining member, and wherein the injection needle cartridge is configured so that the injection needle of the retaining member penetrates through and projects from the airtight member.

11. The injection needle cartridge according to claim 8, wherein
in each of the holder members, a convex part projecting on the inner periphery side toward the outer peripheral surface of the retaining member is formed on at least either one of the slider sections; and
the retaining member has an advance/retreat restricting part capable of restricting the maximum axial separation distance of the paired holder members by means of the engagement with the convex part formed on each of the holder members.

12. The injection needle cartridge according to claim 8, wherein
the injection needle cartridge comprises an applicator including a substantially cylindrical first member provided with an engagement part engaging with an injector on which the injection needle cartridge is to be mounted and a second member which is provided with a hollow part for allowing the first member to be inserted and advances and retreats in the axial direction with respect to the first member, the applicator being formed so as to be capable of accommodating the paired holder members and the retaining member integrally; and
the applicator is configured so that the paired holder members can be turned relative to each other by turning the second member relative to the first member, and the containing space can be retracted axially by the advance and retreat of the second member with respect to the first member.

13. An injector comprising:
(a) an injection needle cartridge comprising:
a substantially columnar retaining member for retaining an injection needle axially penetrating therethrough so that the injection needle projects from both end surfaces thereof;
a first holder member having a first bottom plate facing to one end surface of the retaining member and a first slider section erected from the first bottom plate so as to be in contact with the outer peripheral side surface of the retaining member to hold the retaining member;
a second holder member having a second bottom plate facing to the other end surface of the retaining member and a second slider section erected from the second bottom plate so as to be in contact with the outer peripheral side surface of the retaining member to hold the retaining member, wherein the second holder member is configured to contain the retaining member in a containing space formed by the first bottom plate and the second bottom plate oriented to face to each other, and to be rotatable relative to the first holder member about the axis of the retaining member; and a substantially cylindrical inner ring constituting a rotation restricting mechanism for restricting the relative rotation of the paired holder members in a state of being placed around the retaining member and being positioned on the inner periphery side of the first or second slider section, wherein the containing space is axially retractable in the state in which the slider sections are alternately displaced along the outer periphery of the retaining member to allow the injection needle of the retaining member to penetrate through and to project from the bottom surface plates to be capable of an injection;

wherein the containing space is axially extendable to place the injection needle in the containing space after the injection, in which the cylindrical inner ring is configured to,
  (i) allow the first and second holder members to rotate relative to each other to a position where the extreme end faces of the slider sections of the first and second holder members face to each other, and then
  (ii) restrict the relative rotation of the first and second holder members in said position;

(b) a body part which contains a medicine and is provided with a front end surface for allowing one side of the injection needle of the injection needle cartridge to be pierced; and (c) a cap section which is a bottomed substantially cylindrical member placed around the front end side of the body part and is provided with a through hole for allowing the other side of the injection needle of the internally accommodated injection needle cartridge to penetrate through, wherein the cap section is configured to enable the paired holder members to turn relative to each other and to be capable of advancing and retreating to axially retract the containing space with respect to the body part.

14. The injector according to claim 13, wherein the injector is provided with a storage section for storing a spare injection needle cartridge.

15. An injector comprising:
(a) an injection needle cartridge comprising:
  a substantially columnar retaining member for retaining an injection needle axially penetrating therethrough so that the injection needle projects from both end surfaces thereof;
  a first holder member having a first bottom plate facing to one end surface of the retaining member and a first slider section erected from the first bottom plate so as to be in contact with the outer peripheral side surface of the retaining member to hold the retaining member;
  a second holder member having a second bottom plate facing to the other end surface of the retaining member and a second slider section erected from the second bottom plate so as to be in contact with the outer peripheral side surface of the retaining member to hold the retaining member, wherein the second holder member is configured to contain the retaining member in a containing space formed by the first bottom plate and the second bottom plate oriented to face to each other, and to be rotatable relative to the first holder member about the axis of the retaining member; and
  a substantially cylindrical surrounding ring constituting a rotation restricting mechanism for restricting the relative rotation of the paired holder members in a state of being placed around the first and second slider sections, wherein the containing space is axially retractable in the state in which the slider sections are alternately displaced along the outer periphery of the retaining member to allow the injection needle of the retaining member to penetrate through and to project from the bottom surface plates to be capable of an injection;

wherein the containing space is axially extendable to place the injection needle in the containing space after the injection, in which the cylindrical surrounding ring is configured to,
  (i) allow the first and second holder members to rotate relative to each other to a position where the extreme end faces of the slider sections of the first and second holder members face to each other, and then
  (ii) restrict the relative rotation of the first and second holder members in said position;

(b) a body part which contains a medicine and is provided with a front end surface for allowing one side of the injection needle of the injection needle cartridge to be pierced; and (c) a cap section which is a bottomed substantially cylindrical member placed around the front end side of the body part and is provided with a through hole for allowing the other side of the injection needle of the internally accommodated injection needle cartridge to penetrate through, wherein the cap section is configured to enable the paired holder members to turn relative to each other and to be capable of advancing and retreating to axially retract the containing space with respect to the body part.

16. The injector according to claim 15, characterized by being provided with a storage section for storing a spare injection needle cartridge.

* * * * *